(12) United States Patent
Slukvin et al.

(10) Patent No.: US 8,846,395 B2
(45) Date of Patent: Sep. 30, 2014

(54) GENERATION OF MATURE MYELOMONOCYTIC CELLS THROUGH EXPANSION AND DIFFERENTIATION OF PLURIPOTENT STEM CELL-DERIVED LIN$^-$CD34$^+$CD43$^+$CD45$^+$ PROGENITORS

(75) Inventors: Igor I. Slukvin, Verona, WI (US); Kyung-Dal Choi, Madison, WI (US); Maksym A. Vodyanyk, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 476 days.

(21) Appl. No.: 12/586,600

(22) Filed: Sep. 24, 2009

(65) Prior Publication Data

US 2010/0081199 A1  Apr. 1, 2010

Related U.S. Application Data

(63) Continuation-in-part of application No. 11/520,871, filed on Sep. 14, 2006, now Pat. No. 8,034,613, and a continuation-in-part of application No. 11/443,608, filed on May 31, 2006, now Pat. No. 7,811,821.

(60) Provisional application No. 61/100,313, filed on Sep. 26, 2008, provisional application No. 61/194,421, filed on Sep. 26, 2008, provisional application No. 60/717,168, filed on Sep. 15, 2005, provisional application No. 60/686,145, filed on Jun. 1, 2005.

(51) Int. Cl.

| | |
|---|---|
| *C12N 5/00* | (2006.01) |
| *C12N 5/0787* | (2010.01) |
| *C12N 5/0786* | (2010.01) |
| *C12N 5/0784* | (2010.01) |
| *C12N 5/078* | (2010.01) |

(52) U.S. Cl.
CPC .......... *C12N 5/0642* (2013.01); *C12N 2501/23* (2013.01); *C12N 2501/185* (2013.01); *C12N 2502/1394* (2013.01); *C12N 2506/02* (2013.01); *C12N 2501/22* (2013.01); *C12N 2501/25* (2013.01); *C12N 2500/99* (2013.01); *C12N 2500/38* (2013.01); *C12N 5/0645* (2013.01); *C12N 5/0639* (2013.01); *C12N 2506/45* (2013.01); *C12N 2533/30* (2013.01); *C12N 5/0643* (2013.01); *C12N 2501/15* (2013.01)
USPC ............ 435/377; 435/385; 435/386; 435/387

(58) Field of Classification Search
None
See application file for complete search history.

(56) References Cited

PUBLICATIONS

Wickenhauser et al., Hematopoietic stem cells of the human. Function and morphology, Pathologe 16(1):1-10, 1995 (One page of abstract in English provided).*
Wickenhauser et al. CD34+ human hemopoietic progenitor cells of the bone marrow differ from those of the peripheral blood: an immunocytochemical and morphometric study, Acta Haematol. 93(2-4):83-90, 1995.*
Metcalf et al. "Hematopoietic cytokines." (2008) 111: pp. 485-491.*
Caux et al. "GM-CSF and TNF-α cooperate in the generation of dendritic Langerhans cells." Nature (1992) 360: pp. 258-261.*
Paul et al. "Cooperative effects of interleukin-3 (IL-3), IL-5, and granulocyte macrophage colony-stimulating factor: a new myeloid cell line inducible to eosinophils." Blood (1993) 81: pp. 1193-1199.*
Smith et al. "Expansion of neutrophil precursors and progenitors in suspension cultures of CD34+ cells enriched from human bone marrow." Exp Hematol. (1993), 21(7): pp. 870-877.*
Choi et al., "Generation of mature human myelomonocytic cells through expansion and differentiation of pluripotent stem cell-derived lin-CD34+CD43+CD45+ progenitors," J. Clin. Invest., 119:2818-2829, 2009.
Vodyanik et al., "Human embryonic stem cell-derived CD34+ cells: efficient production in the coculture with OP9 stromal cells and analysis of lymphohematopoietic potential", Blood, 105:617-626, 2005.
Vodyanik et al., "Leukosialin (CD43) defines hematopoietic progenitors in human embryonic stem cell differentiated cultures," Blood, 108:2095-2105, 2006.
Choi, et al., "Hematopoietic and endothelial differentiation of human induced pluripotent stem cells," Stem Cells, 27:559-567, 2009.
Lieber et al., The in vitro production and characterization of neurtophils from embryonic stem cells, Blood, 103:852-859, 2004.
Hamaguchi-Tsuru, et al., "Development and functional analysis of eosinophils from stem cells," Br. J. Haematol., 124:819-827, 2004.
Senju, et al., "Generation and genetic modification of dendritic cells derived from mouse embryonic stem cells," Blood, 101:3501-3508, 2003.
Hino, et al., "Ex vivo expansion of mature human neutrophils with normal functions from purified peripheral blood CD34+ haematopoietic progenitor cells," Br. J. Haematol., 109:314-321, 2000.
Haylock, et al., "Ex vivo expansion and maturation of peripheral blood CD34+ cells into the myeloid lineage," Blood, 80:1405-1412, 1992.
Smith, et al., "Expansion of neutrophil precursors and progenitors in suspension cultures of CD34+ cells enriched from human bone marrow, " Exp. Hematol. 21:870-877, 1993.
Rosenburg, et al., "Characterization of eosinphils generated in vitro from CD34+ peripheral blood progenitor cells," Exp. Hematol, 24:888-893, 1996.
Thavarajah, et al., "1,25(OH)2D3 induces differentiation of osteoclast-like cells from human bone marrow cultures," Biochem. Biophys. Res. Commun., 176:1189-1195, 1991.
MacDonald, et al., "Formation of multinucleated cells that respond to osteotropic hormones in long term human bone marrow cultures," Endocrinology, 120:2326-2333, 1987.

(Continued)

*Primary Examiner* — Deborah Crouch
*Assistant Examiner* — Titilayo Moloye

(57) ABSTRACT

A method for efficient generation of neutrophils, eosinophils, macrophages, osteoclasts, dendritic cells an Langerhans cells from human embryonic stem cells is disclosed.

24 Claims, 12 Drawing Sheets

(5 of 12 Drawing Sheet(s) Filed in Color)

(56) References Cited

PUBLICATIONS

Caux, et al., "CD34+ hematopoietic progenitors from human cord blood differentiate along two independent dendritic cell pathways in response to GM-CSF+TNF alpha," J. Exp. Med., 184:695-706, 1996.

Karlsson, et al., "Homogeneous monocytes and macrophages from human embryonic stem cells following coculture-free differentiation in M-CSF and IL-3," Exp. Hematol., 36:1167-1175, 2008.

Slukvin, et al., "Directed differentiation of human embryonic stem cells into functional dendritic cells through the myeloid pathway," J. Immunol., 176:2924-2932, 2006.

Su, et al., "Differentiation of human embryonic stem cells into immunostimulatory dendritic cells under feeder-free culture conditions," Clin. Cancer Res., 14:6207-6217, 2008.

Senju, et al., "Genetically manipulated human embryonic stem cell-derived dendritic cells with immune regulatory function," Stem Cells, 25:2720-2729, 2007.

Saeki, et al., "A feeder-free and efficient production of functional neutrophils from human embryonic stem cells," Stem Cells, 27:59-67, 2008.

Fairchild, et al., Directed differentiation of dendritic cells from mouse embryonic stem cells. Curr. Biol. 10:1515-1518, 2000.

Yamane, et al., Development of osteoclasts from embryonic stem cells through a pathway that is c-fms but not c-kit dependent. Blood. 90:3516-3523, 1997.

\* cited by examiner

GENERATION OF MATURE MYELOMONOCYTIC CELLS THROUGH EXPANSION AND DIFFERENTIATION OF PLURIPOTENT STEM CELL-DERIVED LIN⁻CD34⁺CD43⁺CD45⁺PROGENITORS

CROSS-REFERENCE TO RELATED APPLICATION

This application claims the benefit of U.S. provisional Application No. 61/100,313 filed Sep. 26, 2008, and U.S. provisional Application No. 61/194,421 filed Sep. 26, 2008. Both of these applications are incorporated by reference herein. Furthermore, this application is a continuation-in-part of U.S. application Ser. No. 11/520,871 filed on Sep. 14, 2006 and issued as U.S. Pat. No. 8,034,613 on Oct. 11, 2011, which in turn (a) claims the benefit of U.S. provisional Application No. 60/717,168 filed on Sep. 15, 2005, and (b) is a continuation-in-part of U.S. application Ser. No. 11/443,608 filed on May 31, 2006 and issued as U.S. Pat. No. 7,811,821 on Oct. 12, 2010, which itself claims priority to U.S. provisional Application No. 60/686,145 filed on Jun. 1, 2005.

STATEMENT REGARDING FEDERALLY SPONSORED RESEARCH OR DEVELOPMENT

This invention was made with government support under HL085223 and HD044067 awarded by the National Institutes of Health. The government has certain rights in the invention.

BACKGROUND OF THE INVENTION

Myeloid cells originate from multipotent hematopoietic stem cells in the bone marrow and consist of granulocytes (neutrophils, eosinophils, basophils) and cells of monocyte/macrophage lineage including dendritic cells (DCs) and osteoclasts. These cells play a critical role in innate and adaptive immunity, inflammatory reactions, and bone remodeling. Transformed myeloid cells give rise to neoplasia, such as acute and chronic myeloid leukemia. Substantial gains in the understanding of myeloid cell development and leukemogenesis have been made over the past several decades through identification, isolation, and targeted manipulation of hematopoietic stem cells and progenitors (Rosmarin, A. G., et al., 2005, Exp. Hematol. 33:131-143. Rosenbauer, F. and Tenen, D. G. 2007, Nat. Rev. Immunol. 7:105-117.). The majority of these studies are based on mouse models because of the ease with which mouse cells can be manipulated and assayed for hematopoietic lineage commitment potential. In vitro differentiation studies using human bone marrow cells are hampered by the limited availability of bone marrow myeloid precursors and the complexity of genetic manipulation of bone marrow cells. While myeloid leukemia cell lines are frequently used to study differentiation of myeloid cells, these cells have a highly abnormal karyotype and often display functional differences from their normal myeloid counterparts (Rado, T. A., et al., 1987, Blood. 70:989-993. Khanna-Gupta, A., et al., 1994, Blood. 84:294-302. Baumann, M. A., et al., 1998, Stem Cells. 16:16-24. Fischkoff, S. A. 1988, Leuk. Res. 12:679-686.).

Human embryonic stem cells (hESCs) are pluripotent stem cells capable of indefinite self-renewal and differentiation toward all three germ layers (ectoderm, endoderm, and mesoderm) (Thomson, J. A., et al. 1998, Science. 282:1145-1147.). In vitro differentiation of hESCs has provided a unique opportunity to study early hematopoietic commitment and specification of different hematopoietic lineages (Keller, G., et al., 1999 Nat. Med. 5:151-152). In addition, establishing conditions for directed differentiation of hESCs toward a particular hematopoietic lineage has allowed the functional analysis of genes essential for lineage expansion and maturation without limitation in terms of cell numbers and heterogeneity of progenitors.

Recently, pluripotent stem cell lines have been obtained from human fibroblasts through insertion of certain genes critical for the maintenance of pluripotency of hESCs (Yu, J., et al. 2007, Science. 318:1917-1920. Takahashi, K., et al. 2007, Cell. 131:861-872. Park, I. H., et al. 2008, Nature. 451:141-146.). These so-called human induced pluripotent stem cells (hiPSCs) behave similarly to hESCs, i.e., they are capable of self-renewal and large-scale expansion and differentiation toward all three germ layers. The hope is that hiPSC lines generated from patients with various diseases could be used to obtain any type of progenitor or differentiated cell carrying a particular genetic trait at the cellular level, thus providing a unique opportunity to analyze disease pathogenesis in vitro.

The Slukvin lab has established a system for efficient hematopoietic differentiation of hESCs into hematopoietic cells through coculture with OP9 bone marrow stromal cells (Vodyanik, M. A., Bork, J. A., Thomson, J. A., Slukvin, I. I. 2005, Blood. 105:617-626) and characterized the two subpopulations of the most primitive multipotent hematopoietic cells to appear in OP9 cocultures of hESCs on the basis of their common expression of CD43 and differential expression of CD45. The lin⁻CD34⁺CD43⁺CD45⁻ cells with broad lymphomyeloid differentiation potential appear first in coculture. Later, lin⁻CD34⁺CD43⁺CD45⁺ cells enriched in myeloid progenitors emerge (Vodyanik, M. A., Thomson, J. A., Slukvin, I. I. 2006, Blood. 108:2095-2105.). Recently the Slukvin lab demonstrated that a similar pattern of hematopoietic differentiation is observed when hiPSCs differentiate into blood cells in coculture with OP9 (Choi, K., et al. 2009, Stem Cells. 27:559-567.).

SUMMARY OF THE INVENTION

The Examples below disclose a method for efficient generation of mature myelomonocytic cells from hESCs and hiPSCs through expansion of lin⁻CD34⁺CD43⁺CD45⁺ myeloid-progenitor enriched multipotent hematopoietic cells with granulocyte/macrophage colony stimulating factor (GM-CSF), followed by their directed differentiation toward neutrophils, eosinophils, macrophages, DCs, Langerhans cells (LCs), and osteoclasts using specific combinations of cytokines and growth factors. The method of the present invention makes it feasible to produce myelomonocytic cells on a large scale. Depending on cell type, $10^7$ to $4 \times 10^9$ mature cells can be obtained from one 6-well plate of hESCs or hiPSCs.

In one embodiment, the present invention is a method of producing myeloid lineage cells, comprising the steps of: (a) obtaining a population of mammalian pluripotent stem cells, preferably human pluripotent stem cells, wherein the stem cells may be derived from mammalian embryos or may be induced pluripotent stem cells, (b) inducing hematopoietic differentiation to obtain lin⁻CD34⁺CD43⁺CD45⁺CD38⁻ multipotent hematopoietic cells, (c) expanding and differentiating lin⁻CD34⁺CD43⁺CD45⁺CD38⁻ cells within the population of the step (b) differentiated cells into more committed myeloid progenitors, and (d) exposing the more committed myeloid progenitors resulting from step (c) to combinations of cytokines and growth factors such that separate population of a cell type selected from the group consisting of neutrophils, eosinophils, macrophages, osteoclasts, dendritic and Langerhans cells is isolated.

In one embodiment, lin$^-$CD34$^+$CD43$^+$CD45$^+$CD38$^-$ multipotent hematopoietic cells are obtained via stroma free embryoid body method, wherein the pluripotent stem cells form embryoid bodies.

In another embodiment, lin$^-$CD34$^+$CD43$^+$CD45$^+$CD38$^-$ multipotent hematopoietic cells are obtained via coculture of the pluripotent stem cells with stromal cells that support hematopoietic differentiation of pluripotent stem cells. Examples of suitable stromal cells include S17, AM20.1B4, UG26.1B6, FH-B-hTERT, primary stromal cells. In a preferred embodiment, OP9 mouse bone marrow stromal cells are used.

Preferably, the existence of lin$^-$CD34$^+$CD43$^+$CD45$^+$CD38$^-$ multipotent hematopoietic cells is confirmed by expression of CD11c, CD15 and CD38 and downregulation of CD34, CD90 and CD117 expression.

Preferably, the expansion differentiation of lin$^-$CD34$^+$CD43$^+$CD45$^+$ cells is allowed for 2-8 days.

In one embodiment, the expansion differentiation of lin$^-$CD34$^+$CD43$^+$CD45$^+$ cells is performed for 2 days. Then the cells are exposed to M-CSF and IL-1β for 1-8 days and populations of macrophages are isolated. Preferably, M-CSF is present at 20±10 ng/mL and IL-1β is present at 10±5 ng/mL. In a more preferred embodiment, the expansion differentiation of lin$^-$CD34$^+$CD43$^+$CD45$^+$ cells is performed for 8 days. The cells are then exposed to M-CSF and IL-1β for 2-3 days and populations of macrophages are isolated.

In another embodiment, the more committed myeloid progenitors are exposed to G-CSF for 7-9 days and populations of neutrophils are isolated. Preferably, G-CSF is present at 100±50 ng/mL.

In yet another embodiment, the more committed myeloid progenitors are exposed to IL-3 and IL-5 for 12-14 days and populations of eosinophils are isolated. Preferably, IL-3 and IL-5 are present at 10±5 ng/mL respectively.

In yet another embodiment, the more committed myeloid progenitors are exposed to GM-CSF and IL-4 for 7-9 days, with TNF-α being added after the first medium change, and populations of dendritic cells are isolated. Preferably, GM-CSF is present at 20±10 ng/mL, IL-4 is present at 20±10 ng/mL and TNF-α is present at 2.5±1 ng/mL.

In yet another embodiment, the more committed myeloid progenitors are exposed to GM-CSF and TGF-β, with TNF-α being added after the first medium change, and populations of Langerhans cells are isolated. Preferably, GM-CSF is present at 20±2 ng/mL, TGF-β is present at 5±2.5 ng/mL and TNF-α is present at 1±0.5 ng/mL.

In yet another embodiment, the more committed myeloid progenitors are exposed to GM-CSF and 1α,25-dihydroxyvitamin D3 for 5-7 days, then GM-CSF, 1α,25-dihydroxyvitamin D3 and RANKL for 7-14 days, and populations of osteoclasts are isolated. Preferably, GM-CSF is present at 100±50 ng/mL for the first 5-7 days and 50±25 ng/mL for the last 7-14 days, 1α,25-dihydroxyvitamin D3 is present at 200±100 nmol and RANKL is present at 10±5 ng/mL. In another embodiment, 1α,25-dihydroxyvitamin D3 is substituted with vitamin D3 like compounds selected from the group consisting of calcitriol, calcidiol, 19-nor-(20S)-1α,25-dihydroxyvitamin D3, and 22-Oxacalcitriol.

In a more preferred embodiment, 1α,25-dihydroxyvitamin D3 is added at the step of expanding and differentiating lin$^-$CD34$^+$CD43$^+$CD45$^+$CD38$^-$ cells, and the resulting more committed myeloid progenitors are exposed to GM-CSF, 1α,25-dihydroxyvitamin D3 and RANKL for 7-14 days. Populations of osteoclasts can then be isolated. In one embodiment, 1α,25-dihydroxyvitamin D3 is substituted with vitamin D3 like compounds selected from the group consisting of calcitriol, calcidiol, 19-nor-(20S)-1α,25-dihydroxyvitamin D3, and 22-Oxacalcitriol.

In another embodiment, the present invention is cells isolated by the methods described above. In one embodiment, the present invention is a population of neutrophils isolated by the above methods, preferably at least 65% pure. In another embodiment, the present invention is a population of eosinophils isolated by the above methods, preferably at least 65% pure. In yet another embodiment, the present invention is a population of macrophages isolated by the above methods, preferably at least 65% pure. In yet another embodiment, the present invention is a population of dendritic cells isolated by the above methods, preferably at least 65% pure. In yet another embodiment, the present invention is a population of Langerhans cells isolated by the above methods, preferably at least 65% pure. In yet another embodiment, the present invention is a population of osteoclasts isolated by the above methods, preferably at least 65% pure.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Cytochemical staining for eosinophil-specific (cyanide-resistant) peroxidase of hESC-derived eosinophils (scale bar: 50 µm; inset, 10 µm). (J) Cytochemical staining for TRAP of hESC-derived osteoclasts (scale bar: 300 µm; inset, 100 µm). Phase-contrast (K) and corresponding DAPI staining (L) of osteoclasts to demonstrate multinucleation (scale bar: 200 µm).

Figure 4:
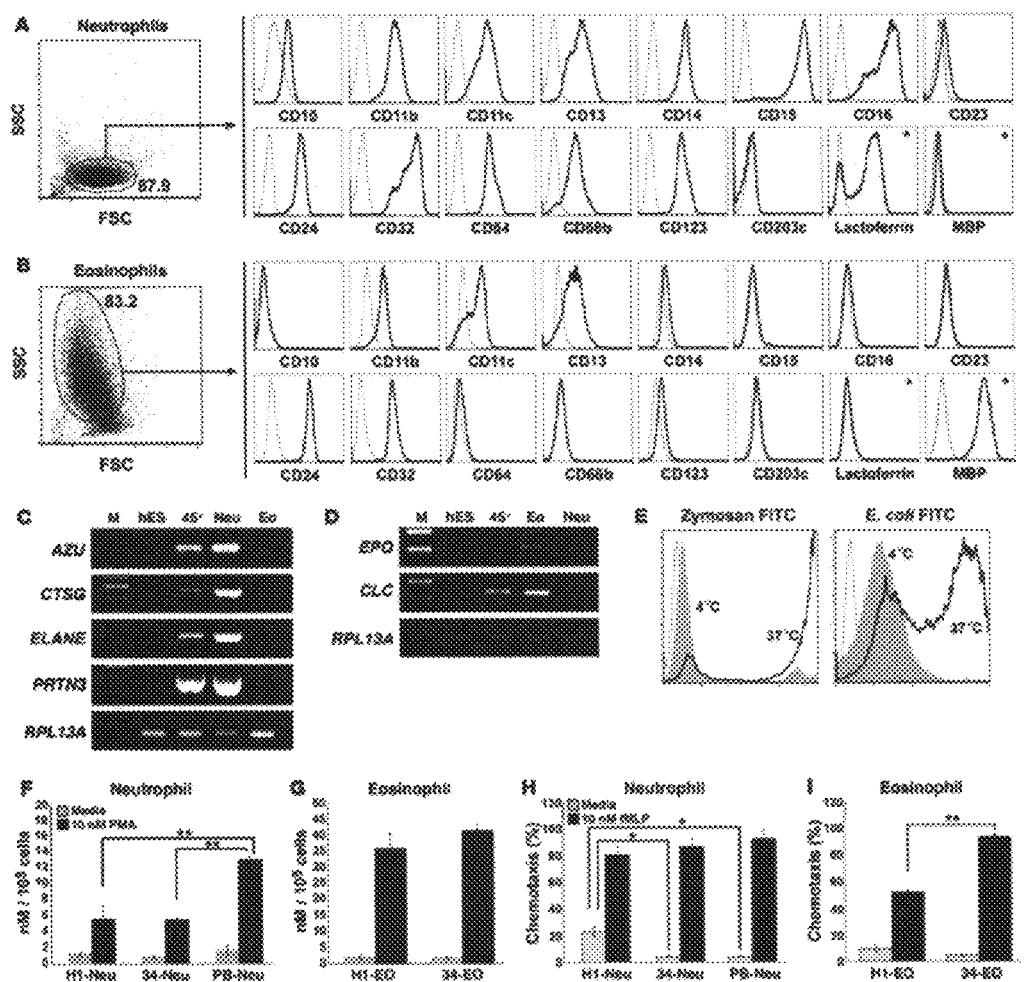

FIG. 4 shows phenotypic, molecular, and functional analysis of H1 hESC-derived eosinophils and neutrophils obtained from isolated CD235a/CD41a$^-$CD45$^+$ cells after 2 days expansion with GM-CSF. Panels A and B show FACS analysis of phenotype of hESC-derived neutrophils (A) and eosinophils (B). Plots show isotype control (gray) and specific antibody (black) histograms; asterisks indicate intracellular staining. Values within dot plots indicate the percentage of cells within the corresponding gate. A representative of 10 independent experiments is shown. By "representative" we mean there is no meaningful variation in the experiments. Panels C and D show analysis of neutrophil and eosinophil-specific gene expression in hESC-derived neutrophils (C) and eosinophils (D) by RT-PCR. M, molecular weight markers; hES, undifferentiated hESCs; 45$^+$, hESC-derived CD235a/CD41a$^-$CD45$^+$ cells isolated after 2 days expansion with GM-CSF; Neu, neutrophils; Eo is eosinophils. (E) Phagocytosis of zymosan and $E.$ $coli$ particles by hESC-derived neutrophils. Plots show histograms for isotype control (open gray) and cells incubated at 4° C. (filled gray; nonspecific binding control) and 37° C. (open black). (F) Superoxide production by hESC-derived (H1-Neu), somatic CD34$^+$ cell-derived (34-Neu), and peripheral blood (PB-Neu) neutrophils in response to phorbol myristate acetate (PMA). Results are mean±SEM of 3 independent experiments performed in triplicate; **P<0.01. (G) Superoxide production by hESC-derived (H1-EO) and somatic CD34$^+$ cell-derived (34-EO) eosinophils in response to PMA. Results are mean±SEM of 3 independent experiments performed in triplicate. (H) Chemotactic activity of hESC-derived, somatic CD34$^+$ cell-derived, and peripheral blood neutrophils. Results are mean±SEM of 3 independent experiments performed in triplicate; *P<0.05. (I) Chemotactic activity of hESC-derived and somatic CD34$^+$ cell-derived eosinophils. Results are mean±SEM of 3 independent experiments performed in triplicate; **P<0.01.

Figure 5:
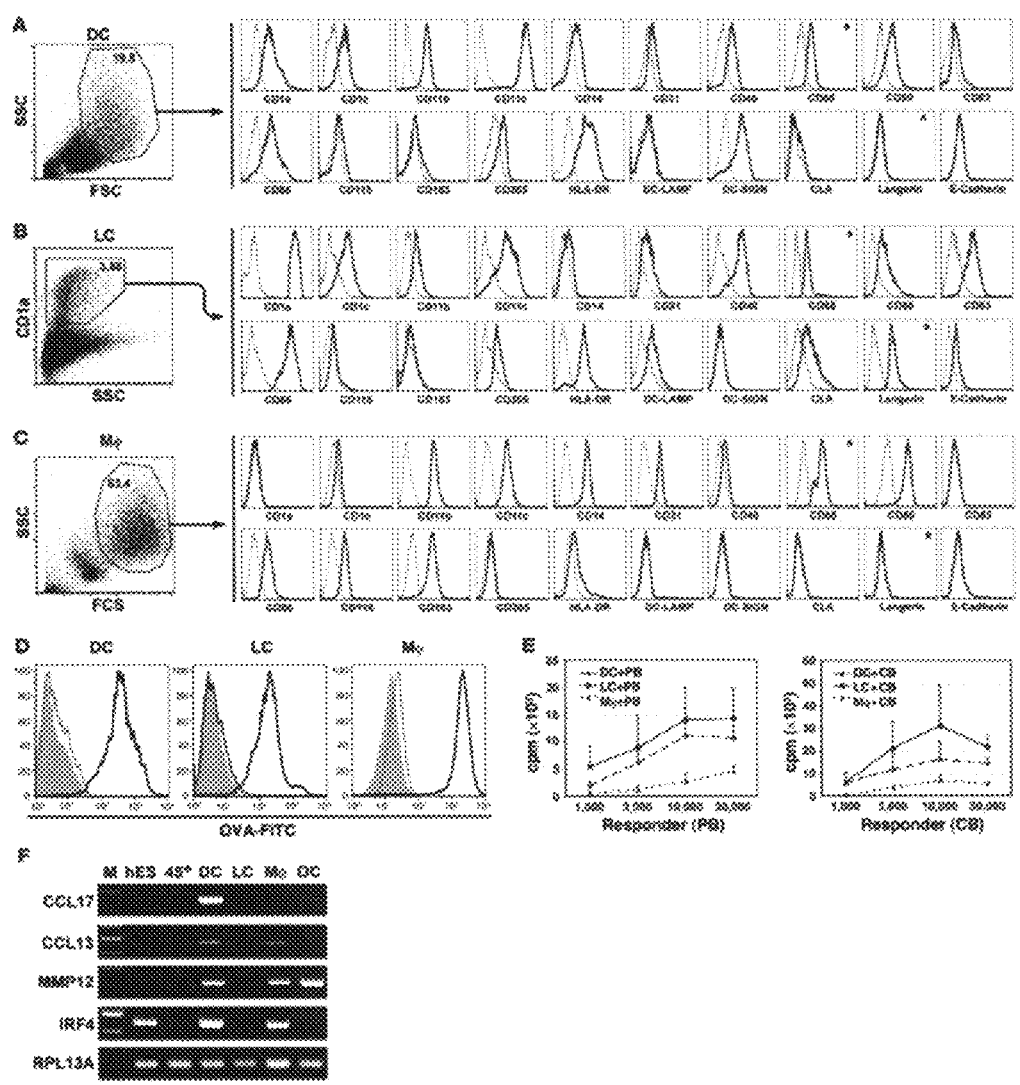

FIG. 5 shows phenotypic, molecular, and functional analysis of H1 hESC-derived DCs, LCs, and macrophages obtained from isolated CD235a/CD41a$^-$CD45$^+$ cells after 2 days expansion with GM-CSF. FACS analysis of hESC-derived DCs (A), LCs (B), and macrophages (C). Plots show isotype control (gray) and specific antibody (black) histograms; asterisks indicate intracellular staining. Values within dot plots indicate the percentage of cells within the corresponding gate. A representative of 5-10 independent experiments is shown. By "representative" we mean there is no meaningful variation in the experiments. (D) FACS analysis of OVA uptake and processing by hESC-derived antigen-presenting cells. Plots show isotype control (open gray), cells incubated at 4° C. (filled gray; nonspecific binding control), and 37° C. (open black) histograms. (E) Allogeneic stimulatory capacity of hESC-derived antigen-presenting cells. PB, peripheral blood lymphocytes; CB, cord blood lymphocytes. Results are mean±SEM of 3 independent experiments performed in triplicate. (F) RT-PCR analysis of gene expression in hESC-derived antigen-presenting cells. Mφ, macrophages; OC, osteoclasts.

Figure 6:
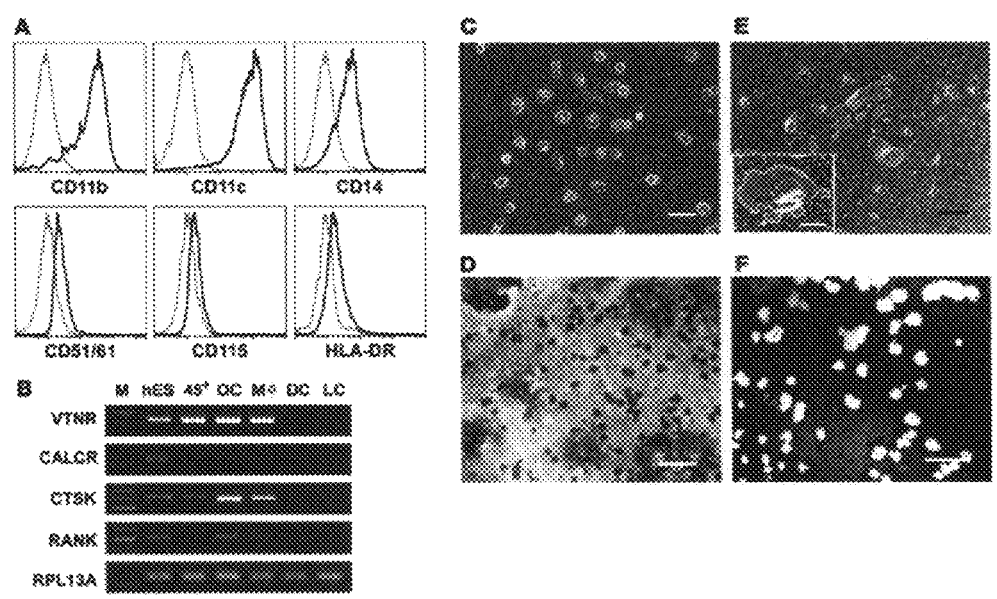

FIG. 6 shows phenotypic, molecular, and functional analysis of H1 hESC-derived osteoclasts. (A) FACS analysis of hESC-derived osteoclasts. A representative of 3 independent experiments is shown. By "representative" we mean there is no meaningful variation in the experiments. (B) RT-PCR analysis of gene expression in hESC-derived osteoclasts. Analysis of mineralized matrix-resorptive capacity of hESC-derived macrophages (C and D) and osteoclasts (E and F) using BioCoat osteologic discs. Resorption lacunae around multinucleated cells are clearly visible in osteoclast cultures (E, inset) but not in cells cultured with macrophage colony-stimulating factor (M-CSF) and IL-1β (C). Visualization of resorption lacunae in macrophage (D) and osteoclast (F) cultures with von Kossa staining. Scale bar: 200 µm (C-F).

Figure 7:
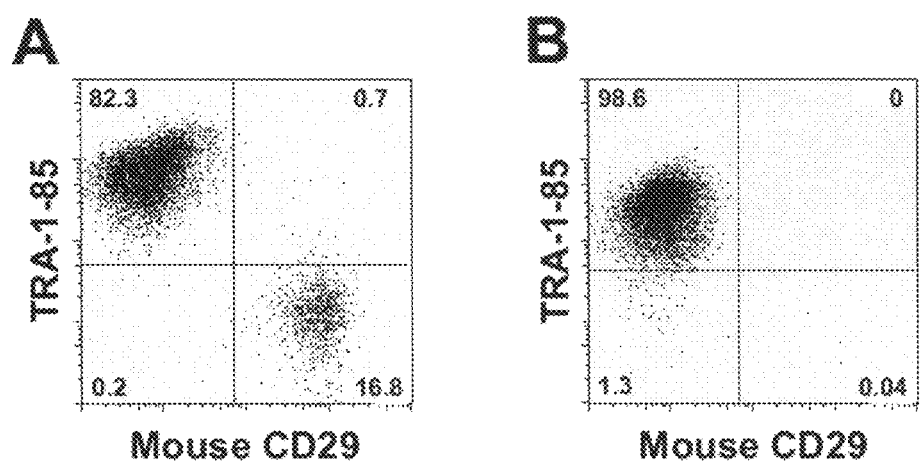

FIG. 7 shows evaluation of content of human and mouse cells in day 9 hESC/OP9 cocultures (A) and Percoll-isolated cells collected after expansion of coculture cells with GM-CSF for two days (B). Human cells were identified using TRA-1-85-APC monoclonal antibody (R&D Systems Inc., Minneapolis, Minn.) which detects the OK, a blood group antigen expressed by virtually all human cells (Williams B. P., et al. $Immunogenetics$ 1988; 27:322-329). Mouse stromal cells were detected with mouse-specific CD29 antibodies (Serotec, Oxford, UK).

Figure 8:
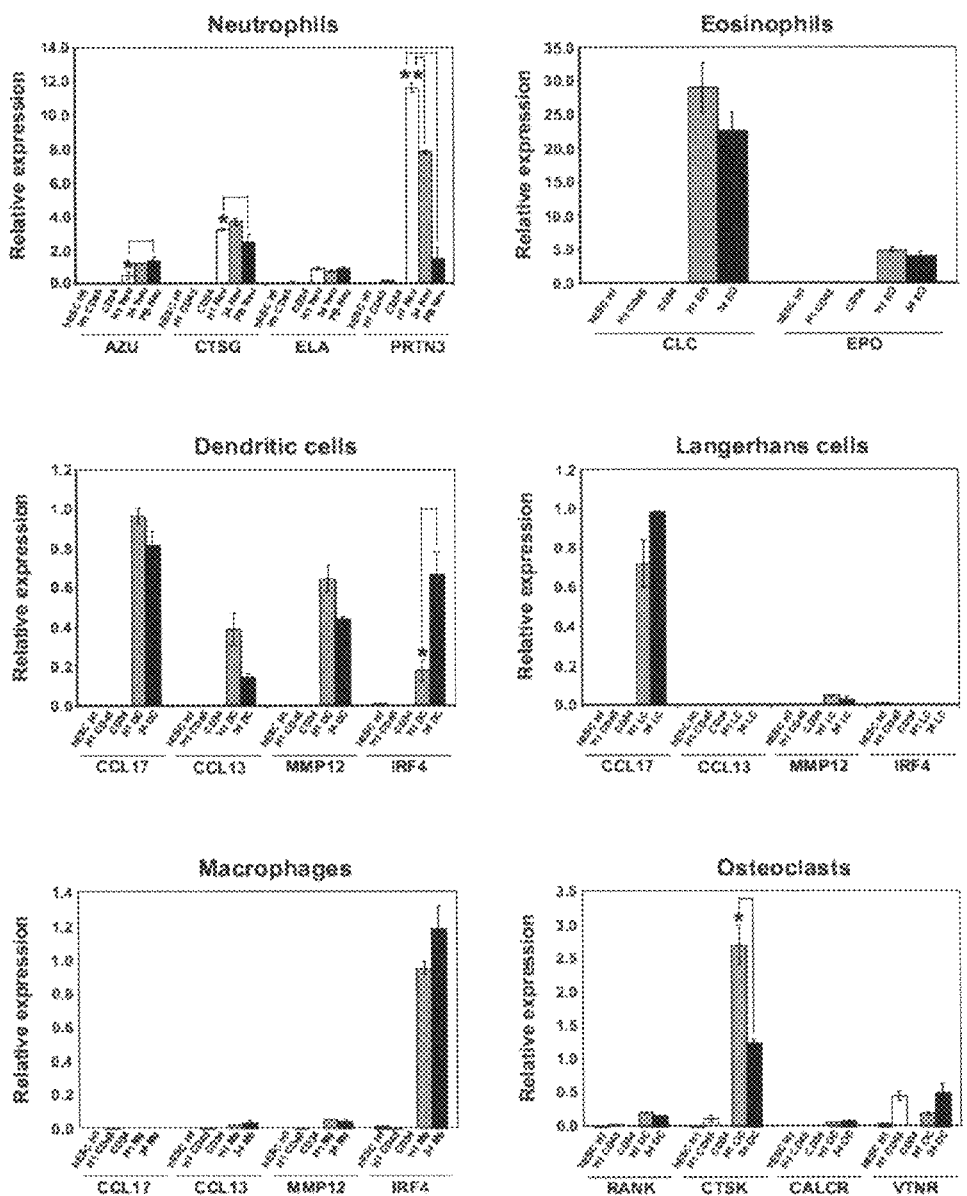

FIG. 8 shows quantitative real time PCR analysis of expression of indicated genes in undifferentiated hESCs (hES H1), CD235a/CD41a$^-$CD45$^+$ cells derived from hESCs after 2 days expansion with GM-CSF ($H_1$CD45), somatic CD34$^+$ cells (CD34), and neutrophils (Neu), eosinophils (EO), dendritic cells (DC), Langerhans cells (LC), macrophages (Mφ), and osteoclasts (OC) derived from hESC(H1), somatic CD34$^+$ cells (CD34), or peripheral blood (PB). Results are mean±SE of two experiments performed in triplicate; *p<0.05, **p<0.01.

Figure 9:
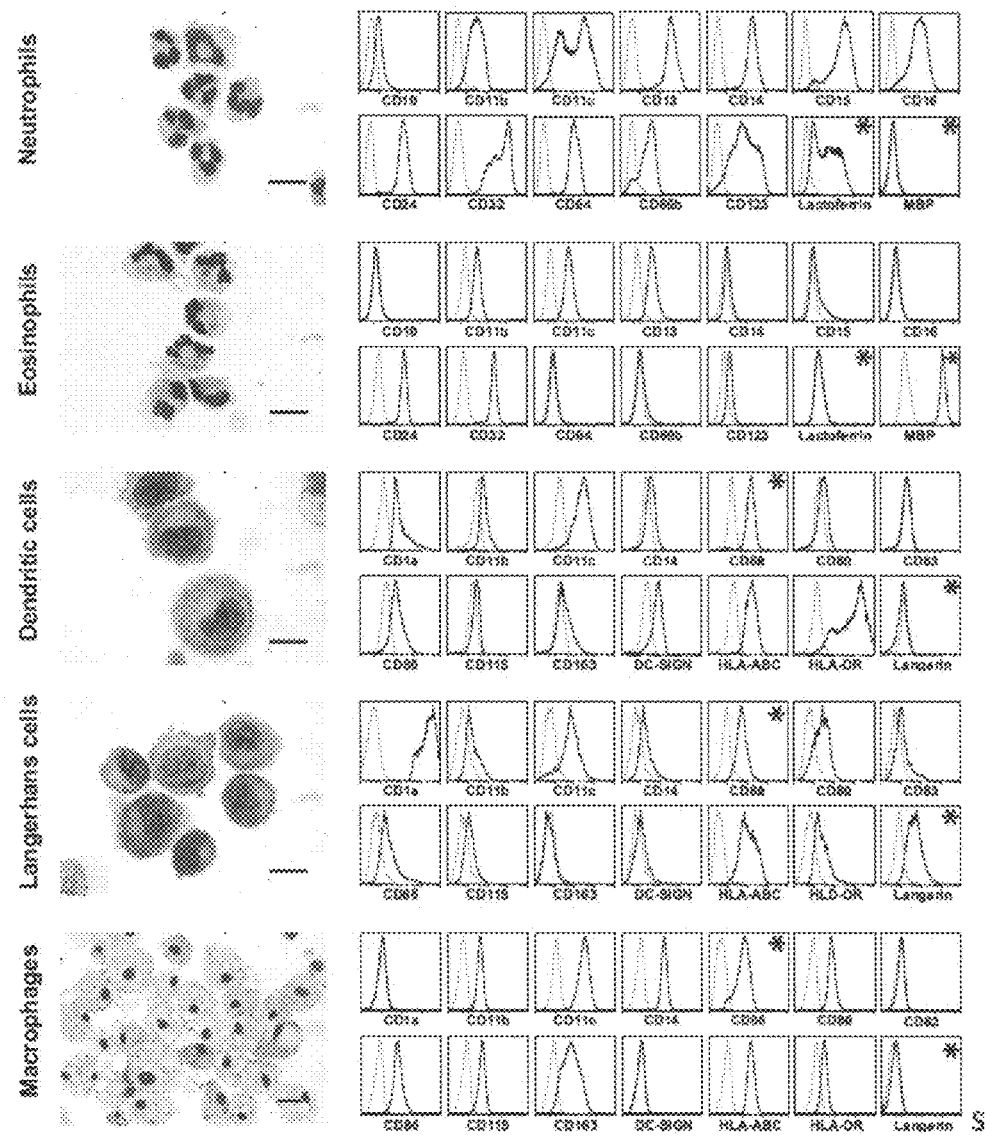

FIG. 9 shows morphology and phenotypic analysis of neutrophils, eosinophils, LCs and DCs obtained from iPS(foreskin)-1 line. Left panels show Wright stained cytospins of corresponding cells; scale bar is 10 µm (neutrophils, eosinphils, DCs and LCs) and 200 µm (macrophages). Right panels show FACS analysis of phenotype of hiPSC-derived neutrophils, eosinophils, DCs and LCs. Plots show isotype control (open gray) and specific antibody (open black) histograms; *indicates intracellular staining.

Figure 10:
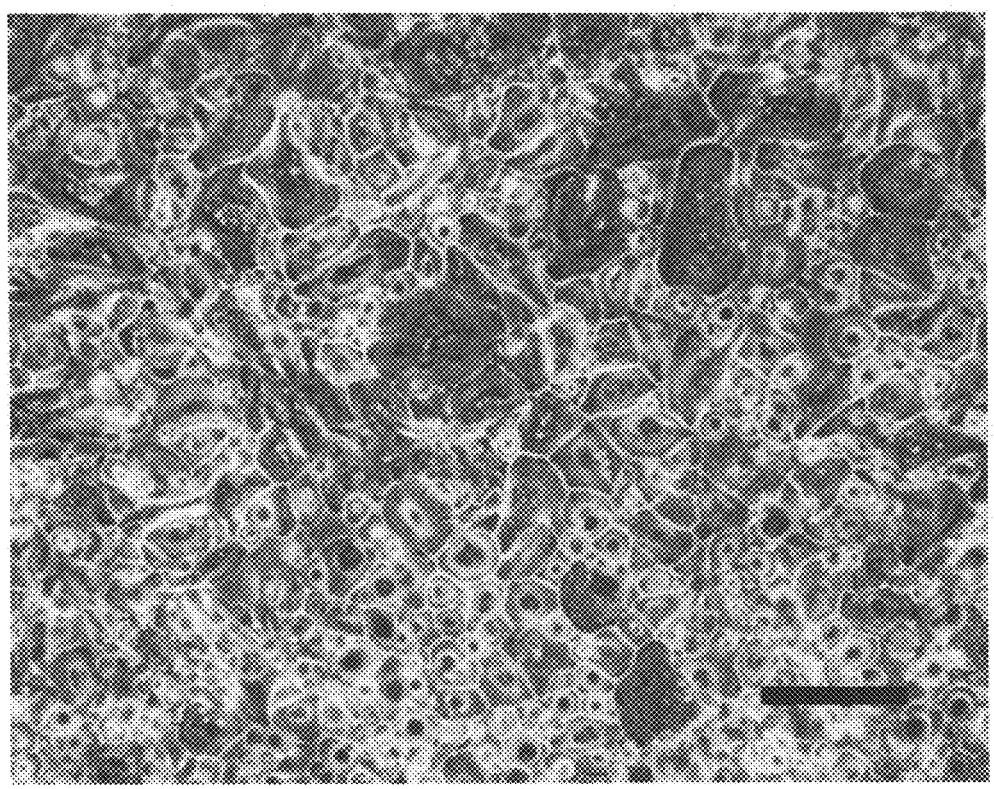

FIG. 10 shows cytochemical staining for TRAP of iPS (foreskin)-1 derived osteoclasts (scale bar is 200 µm).

Figure 11:
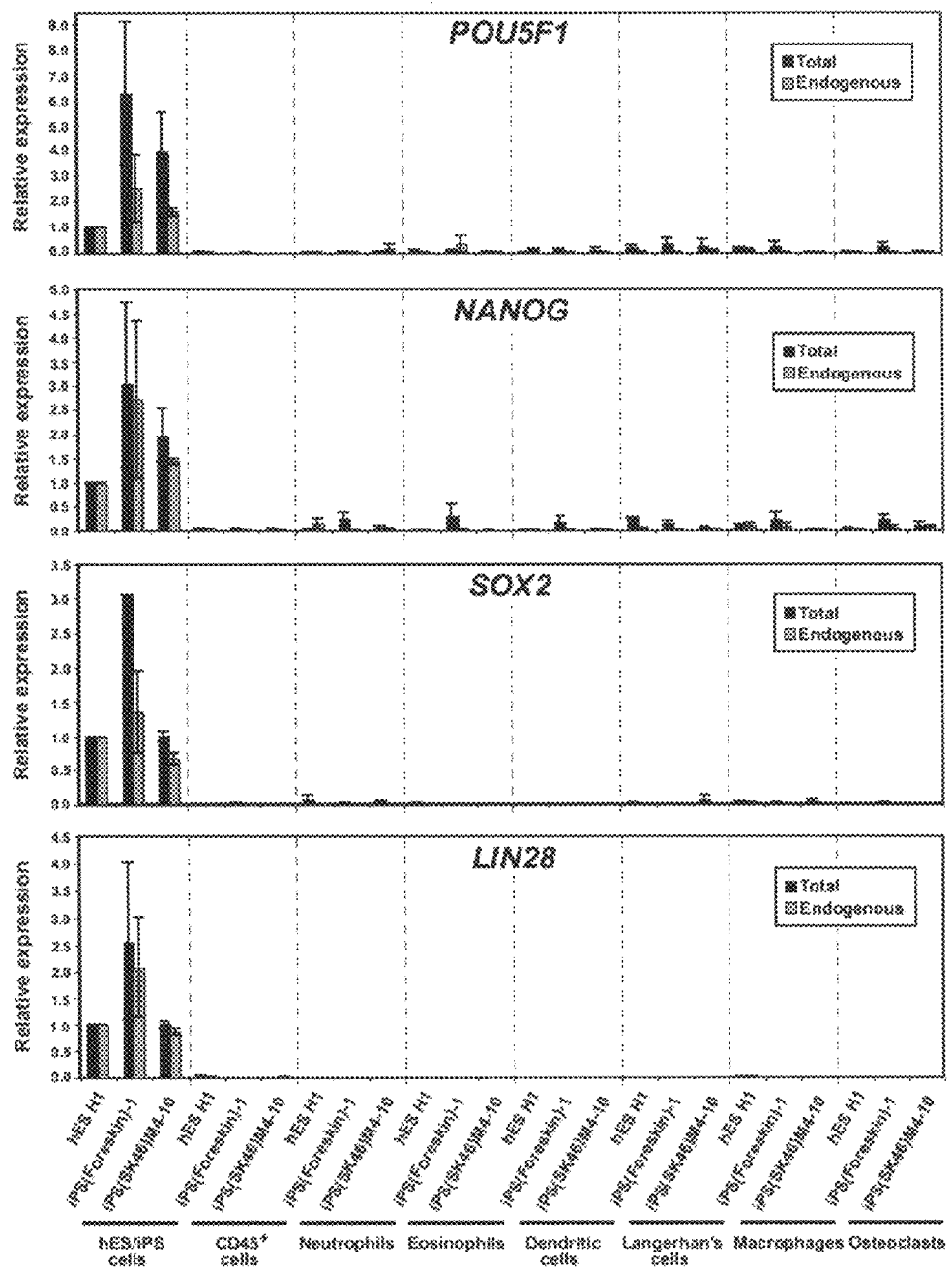

FIG. 11 shows quantitative real time PCR analysis of total and endogenous expression of key pluripotency genes in undifferentiated hiPSCs obtained through reprogramming of human foreskin (iPS(Foreskin)-1) and adult (iPS(SK46)M4-10) fibroblasts and hiPSC-derived CD235a/CD41a$^-$CD45$^+$ cells expanded with GM-CSF for 2 days (CD45+), mature neutrophils, eosinophils, dendritic and Langerhans cells, macrophages and osteoclasts. PCR amplification was performed using primers to amplify endogenous and total POU5F1, NANOG, SOX2, or LIN28 mRNA. The PCR products were normalized with GAPDH of the same samples and compared with hESC H1 as relative standard. Primer sequences and details of PCR procedure have been previously described (Yu J., et al. $Science$, 2007; 318:1917-1920).

Figure 12:
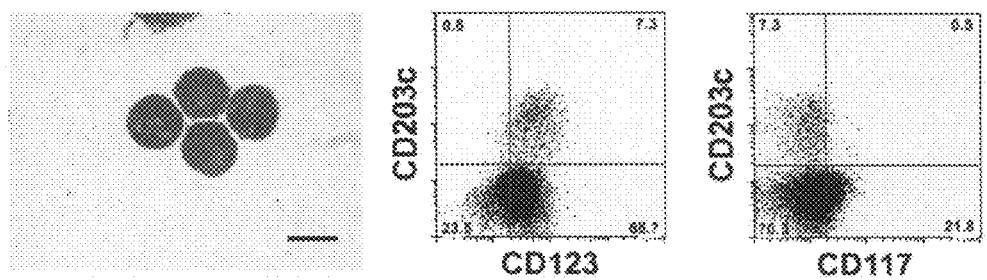

FIG. 12 shows differentiation of peripheral blood CD34$^+$ cells into basophils. Peripheral blood CD34$^+$ cells obtained from healthy adult donor were cultured at 5×10$^4$/ml for 14 days in IMDM (Invitrogen) supplemented with 20% of heat-inactivated FBS (HyClone) in the presence of 10 ng/ml IL-3 and 10 ng/ml of SCF, with a half-medium change every third day. In this culture, cells with typical basophil morphology were generated (left panel shows Wright stain of cytospins, bar is 10 µm). Flow cytometric analysis depicted on the right demonstrated that approximately 7% of the cells generated in this condition had typical mature basophil phenotype $CD203c^+CD123^+CD117^-$.

DESCRIPTION OF THE INVENTION

In one embodiment, the present invention is a method to efficiently produce neutrophils, eosinophils, macrophages, osteoclasts, dendritic and Langerhans cells from mammalian pluripotent stem cells, preferably human embryonic stem cells (hESCs) or induced pluripotent stem cells (iPSCs, see, for example, Yu J, et al., Science 318:1917-1920, 2007, incorporated by reference, for one method of making iPSCs) through differentiation of the hESCs or iPSCs into $lin^-CD34^+CD43^+CD45^+$ myeloid-progenitors enriched cells, followed by expansion of $lin^-CD34^+CD43^+CD45^+$ myeloid-progenitors enriched cells with GM-CSF and subsequent lineage-specific differentiation. $lin^-CD34^+CD43^+CD45^+$ myeloid-progenitors enriched cells can be generated by stroma free embryoid body method or by coculturing the stem cells with stromal cells that support stem cells, preferably generated in stem cell/OP9 coculture. Differentiation is subsequently directed using specific combinations of cytokines and growth factors. Cytokine analogs or small molecules activating corresponding receptors can be used for the same purposes.

Choi, et al. (2009, *J. Clin. Invest.* 119(9): 2818-2829, incorporated by reference) is an academic manuscript authored by the inventors and describes one embodiment of the present invention.

Generation of $lin^-CD34^+CD43^+CD45^+$ Cell Population

In one embodiment, hESCs are cocultured with stromal cells for 8-10 days to induce hematopoietic differentiation and generate $lin^-CD34^+CD43^+CD45^+$ cells that are $CD38^-$. Any stromal cell lines that support hematopoietic differentiation of pluripotent stem cells can be used in the coculture. For example, S17, AM20.1B4, UG26.1B6, FH-B-hTERT, primary stromal cells. In one preferred embodiment, OP9 mouse bone marrow stromal cells are used. Hematopoietic differentiation can be confirmed via flow cytometry by detection of $CD43^+$ cells in the hESC/OP9 coculture. $Lin^-CD34^+CD43^+CD45^+$ cells can also be generated using embryoid body method without stromal cells, or eventually using cellular matrices and 2D cultures. Many methods have been described to generate blood cells from ESCs using embryoid body method. (For examples, see Pick, M., et al. *Stem Cells*, 2007, 25:2206-2214; Chadwick, K., et al. *Blood,* 2003, 102:906-915; Zambidis, E. T., et al. *Blood,* 2005, 106:860-870.) The cells are then dissociated and preferably cultured in α-MEM containing 200±100 ng/mL GM-CSF for 1-8 days to expand $CD45^+$ myeloid progenitors. Similar expansion can be achieved in similar conditions using serum-free SFEM medium supplemented with lipids (1% Ex-Cyte).

Before directed differentiation into mature myeloid lineages, the cells are subjected to Percoll separation and optional further isolation of $CD45^+$ cells.

The $CD45^+$ cells are then subjected to directed differentiation, preferably as described herein.

Generation of Other Cell Types

Neutrophils can be obtained by culturing the $CD45^+$ cells with or without OP9 cells in serum-containing medium in the presence of 100±50 ng/mL granulocyte colony stimulating factor (G-CSF) for 7-9 days.

Eosinophils can be obtained by culturing the $CD45^+$ cells with or without OP9 cells in serum-containing medium in the presence of 10±5 ng/mL IL-3 and 10±5 ng/mL IL-5 for 12-14 days.

Macrophages can be obtained by culturing the cells under low-adherent conditions in serum containing media with 20±10 ng/mL M-CSF and 10±5 ng/mL IL-1β for 1-8 days. By "low-adherent conditions", we mean at least 90% of the cells, preferably 95%, most preferably 99%, grow in suspension and not-attached. In one preferred embodiment, macrophages can be obtained by culturing day 8 $CD45^+$ myeloid progenitors under low-adherent conditions in serum containing media with 20±10 ng/mL M-CSF and 10±5 ng/mL IL-1β for 2-3 days.

Dendritic cells (DCs) can be obtained by culturing the cells, preferably day 8 $CD45^+$ myeloid progenitors, under low-adherent conditions in serum-free medium with 20±10 ng/mL GM-CSF and 20±10 ng/mL IL-4 for 7-9 days, 2.5±1 ng/mL TNF-α being added into the medium after the first medium change (day 3).

Langerhans cells (LCs) can be obtained by culturing the cells under low-adherent conditions in serum-free medium with 20±2 ng/mL GM-CSF and 5±2.5 ng/mL TGF-β for 7-9 days, 1±0.5 ng/mL TNF-α being added into the medium after the first medium change (day 3).

Preferably, the osteoclast differentiation is done in two steps: the cells are cultured in serum-containing medium with 100±50 ng/mL GM-CSF and 200±100 nmol Vitamin D3 under low-adherent conditions for 5-7 days and then transferred into conventional cell culture plates in serum-containing medium with 50±25 ng/mL GM-CSF, 200±100 nmol Vitamin D3 (1α,25-dihydroxyvitamin D3) and 10±5 ng/mL RANKL for another 7-14 days. The first step of osteoclast induction can also be simplified by adding Vitamin D3 directly into the medium at the initiation of the GM-CSF expansion step. Although Vitamin D3 is preferred, other Vitamin-D3-like compounds, such as calcitriol, calcidiol, 19-nor-(20S)-1α,25-dihydroxyvitamin D3, and 22-Oxacalcitriol, can also be used for the same purpose.

Morphologic, phenotypic, molecular and functional analyses show that hESC-derived myeloid cells are comparable with corresponding somatic counterparts.

When one uses the optimized protocol (See Examples, FIG. 1), the purity of neutrophils and eosinophils is at least 80%, macrophages at least 65%, osteoclasts at least 95%, DC at least 70%. For example, in our differentiation system, we obtain populations comprising 70% DCs combined with other differentiated and immature myeloid cells. We can also obtain 10% LCs combined with other differentiated and immature myeloid cells. Since DCs and LCs express CD11a, one can sort these cell populations, respectively, for $CD1a^+$ to obtain DCs and LCs with at least 95% purity. A pure population of macrophages (at least 95% purity) can be obtained simply by placing cells in conventional culture flasks and selecting adherent cells after 2 hour incubation.

The above described approach can also work with embryoid body (EB) or any other differentiation system that forms $CD34^+CD43^+CD45^+$ cells. For example, one may make EBs from pluripotent stem cells via standard protocol. At the stage when maximum generation of colony-forming cells and $CD34^+CD43^+CD45^+$ are observed (equivalent of OP9 coculture day 8-10), one can then dissociate the cells and place them into GM-CSF expansion medium in non-adherent conditions. Starting from this point, one can then use the above-described protocol. By "non-adherent conditions", we mean at least 99% of the cells, preferably 99.5%, grow in suspension and not-attached. Most preferably, all the cells grow in suspension and not-attached.

One may also use the above identified invention to create cells of myeloid lineage from iPSCs. For example, one may obtain iPSCs as described in Yu J, et al., *Science* 318:1917-

1920 (2007), and differentiate them into lin-CD34+CD43+ CD45+ myeloid progenitors enriched cells. Starting from this point, one can then use the above-described protocol.

The present invention has been described above with respect to its preferred embodiments. Other forms of this concept are also intended to be within the scope of the claims.

EXAMPLES

Basic research into human mature myelomonocytic cell function, myeloid lineage diversification and leukemic transformation, and assessment of myelotoxicity in preclinical drug development requires a constant supply of donor blood or bone marrow samples and laborious purification of mature myeloid cells or progenitors, which are present in very small quantities. To overcome these limitations, we have developed a protocol for efficient generation of neutrophils, eosinophils, macrophages, osteoclasts, DCs, and Langerhans cells from human embryonic stem cells (hESCs). As a first step, we generated lin$^-$CD34$^+$CD43$^+$CD45$^+$ hematopoietic cells highly enriched in myeloid progenitors through coculture of hESCs with OP9 feeder cells. After expansion in the presence of GM-CSF, these cells were directly differentiated with specific cytokine combinations toward mature cells of particular types. Morphologic, phenotypic, molecular, and functional analyses revealed that hESC-derived myelomonocytic cells were comparable to their corresponding somatic counterparts. In addition, we demonstrated that a similar protocol could be used to generate myelomonocytic cells from induced pluripotent stem cells (iPSCs). This technology offers an opportunity to generate large numbers of patient-specific myelomonocytic cells for in vitro studies of human disease mechanisms as well as for drug screening.

Short treatment with GM-CSF expands hESC-derived CD235a/CD41a$^-$CD34$^+$CD45$^+$ cells enriched in myeloid CFCs.

Figure 1:
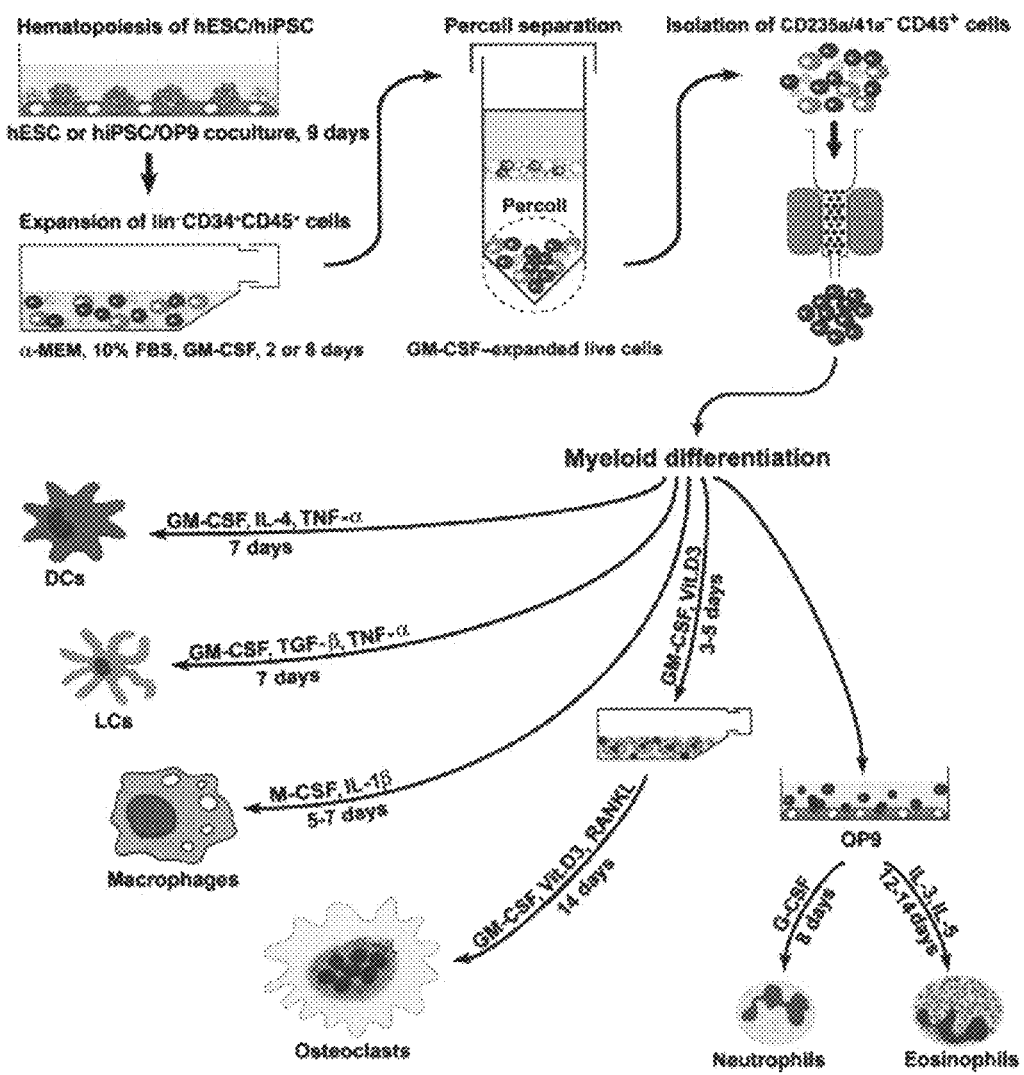
FIG. 1 is a schematic diagram of the differentiation protocol used for myeloid cell generation from hESCs and hiPSCs. Vit.D3, vitamin D3.
Figure 2:
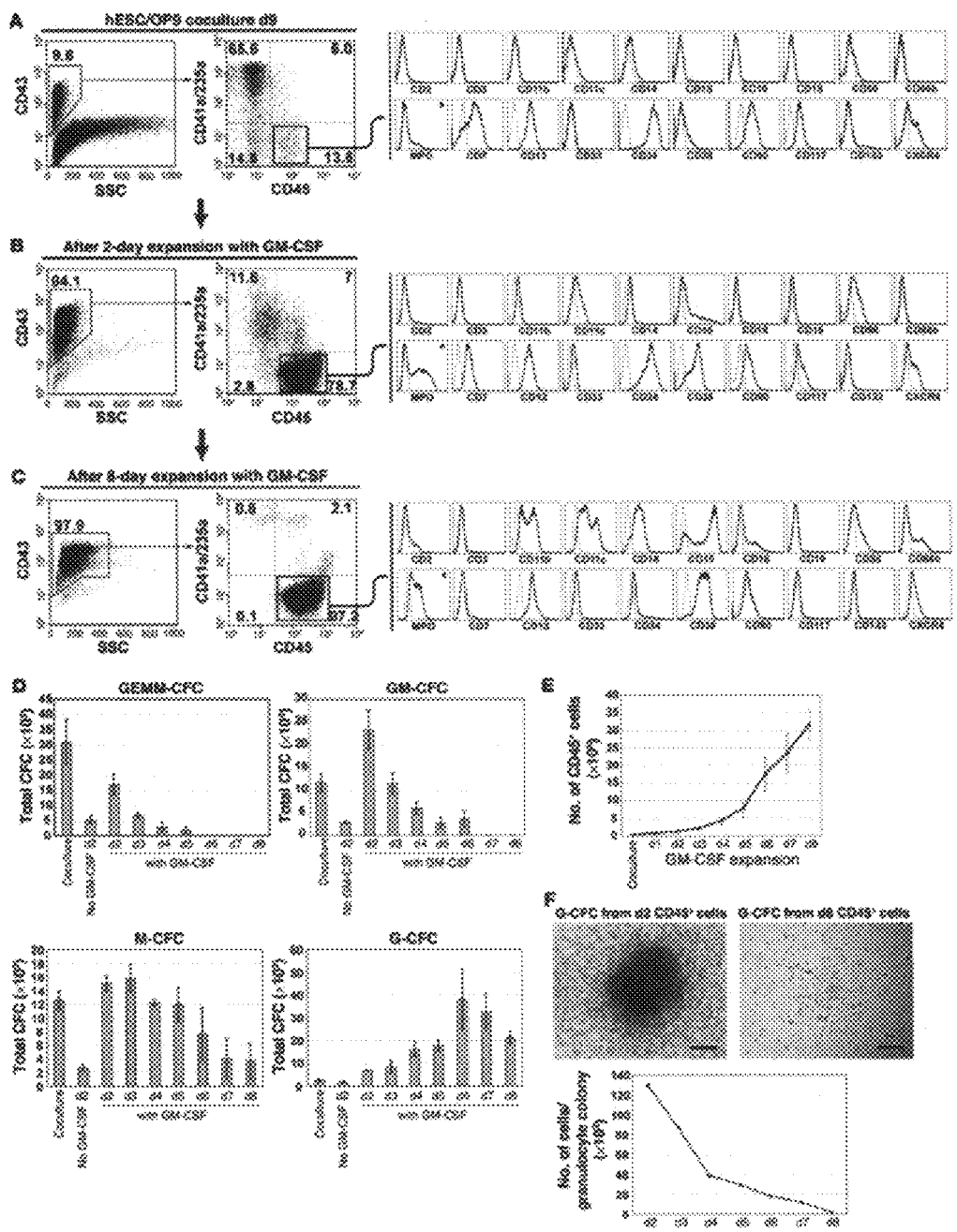
FIG. 2 shows characterization of H1 hESC-derived myeloid progenitors generated in OP9 coculture and expanded with GM-CSF. Phenotype of CD235a/CD41a$^-$CD45$^+$ cells generated on day 9 (d9) of hESC/OP9 coculture (A) and after 2 (B) and 8 days (C) expansion with GM-CSF; the asterisk indicates intracellular staining. A representative of 3-5 independent experiments is shown. By "representative" we mean there is no meaningful variation in the experiments. SSC, side scatter. Values within dot plots indicate the percentage of cells in the respective quadrants. (D) Absolute number of myeloid CFCs generated from one 10-cm dish of hESC/OP9 coculture and from CD235a/CD41a$^-$CD45$^+$ cells obtained from the same dish and expanded in the presence of GM-CSF for 2-8 days. Results are mean±SEM of 3-5 independent experiments. (E) Kinetics of CD235a/CD41a$^-$CD45$^+$ cell expansion with GM-CSF. Data are expressed as the number of CD235a/CD41a$^-$CD45$^+$ cells generated from one 10-cm dish of hESC/OP9 coculture and following expansion with GM-CSF. Results are mean±SEM of 3-5 experiments. (F) Typical morphology of granulocytic colony obtained from CD235a/CD41a$^-$CD45$^+$ cells expanded with GM-CSF for 2 and 6 days (scale bars: 100 μm). The graph shows cell numbers per single granulocytic colony obtained from cells expanded with GM-CSF for 2-8 days.

A schematic diagram of the differentiation protocol is presented in FIG. 1. Hematopoietic differentiation was induced by transferring the hESCs onto OP9 feeders as previously described (Vodyanik, M. A., et al. 2005, *Blood*. 105:617-626. Vodyanik, M. A., and Slukvin, I. I. 2007, *Curr. Protoc. Cell Biol.* Chapter 23, unit 23.6.). On day 9 of coculture, differentiated hESCs were harvested and characterized. As shown in FIG. 2A, three major subsets of hematopoietic cells could be identified on day 9 of hESC/OP9 coculture: CD43$^+$ CD235a$^+$CD41a$^{+/-}$ (erythro-megakaryocytic), lin$^-$CD34$^+$ CD43$^+$CD45$^-$ (multipotent with broad lymphomyeloid potential), and lin$^-$CD34$^+$CD43$^+$CD45$^+$ (myeloid-skewed) cells (Vodyanik, M. A., et al. 2006, *Blood*. 108:2095-2105.). After dissociation and reaggregation of day 9 hESC/OP9 coculture cells in non-adherent conditions, CD45$^+$ cells were expanded by addition of 200 ng/ml GM-CSF. In these cultures, hematopoietic cells were released from aggregates into suspension and could be easily isolated by Percoll-based density gradient centrifugation without an additional enzymatic digestion step starting from day 2 of expansion (FIG. 1). Analysis of kinetics demonstrated that the proportion of CD235a/CD41a$^+$ erythro-megakaryocytic cells decreased following treatment with GM-CSF, while the number of CD235a/CD41a$^-$CD45$^+$ cells increased after 8 days of cultures (FIGS. 2, A, B, C, and E). However, the maximum expansion of bipotential granulocyte-macrophage CFCs (GM-CFCs) and unipotential macrophage CFCs (M-CFCs) within the CD235a/CD41a$^-$CD45$^+$ population was observed on day 2 of culture with GM-CSF (FIG. 2D). At this time, the most primitive myeloid cells, granulocyte/erythrocyte/macrophage/megakaryocyte CFCs (GEMM-CFCs) were also detected in substantial numbers. The total numbers of GEMM-CFCs, GM-CFCs, and M-CFCs gradually decreased after 2-3 days of expansion with GM-CSF. In contrast, the total number of unipotential G-CFCs gradually increased up to 6 days of culture with GM-CSF. However, we noted significant differences in the size of granulocyte colonies at different time points. As shown in FIG. 2F, granulocyte colonies obtained after 2 days of expansion with GM-CSF were much larger and contained up to 70-150 times more cells per single colony as compared with those colonies obtained after 6-8 days of expansion, indicative of a gradual decrease in the proliferative potential of G-CFCs. CD235a/CD41a$^-$CD45$^+$ cells obtained after 2 days expansion with GM-CSF retained CD34 expression and lacked the majority of lineage-specific markers, although upregulation of CD38, myeloperoxidase (MPO), CD15, and CD56 expression and downregulation of CD90 and CD117 expression were apparent (FIG. 2B). On cytospins, these cells displayed typical myeloblast morphology, with cells undergoing mitosis readily apparent (FIG. 3A). At day 8 of GM-CSF expansion, CD45$^+$ cells lost expression of primitive hematopoietic cell markers CD34, CD90, and CD117 and showed conspicuous upregulation of myeloid lineage markers CD11b, CD11c, CD14, CD15, CD16, CD66b, and MPO (FIG. 2C). Most cells displayed promyelocyte and myelocyte morphology, with cells at more advanced stages of maturation and occasional myeloblasts also identified (data not shown). Essentially no contaminating OP9 cells were detected in GM-CSF-expanded cell samples (FIG. 7).

GM-CSF-Expanded CD235a/CD41a$^-$CD34$^+$CD45$^+$ Cells Generate Almost the Entire Spectrum of Mature and Fully Functional Myelomonocytic Cells.

Because CD235a/CD41a$^-$CD34$^+$CD45$^+$ cells after 2 days expansion with GM-CSF showed the highest number of CFCs, we used these cells to develop conditions for obtaining mature myelomonocytic cells from hESCs. To induce differentiation toward neutrophils, we cultured CD235a/CD41a$^-$ CD34$^+$CD45$^+$ cells in serum-containing medium on OP9 cells in the presence of G-CSF. An almost pure population of cells with typical neutrophil morphology (FIG. 3D) and phenotype (FIG. 4A) was generated in this condition after 7-9 days of culture. It should be noted that hESC-derived neutrophils showed a high level of CD14 expression (FIG. 4A). In general, CD14 is considered a marker of monocytes in peripheral blood, although it is well known that CD14 is also expressed on granulocytes, but at a much lower level (Antal-Szalmas, P., et al. 1997, *J. Leukoc. Biol.* 61:721-728. Wright, S. D., et al. 1991, *J. Exp. Med.* 173:1281-1286.). Our data indicate that both granulocytic and monocytic cells generated in vitro express a high level of CD14 and analysis of CD14 expression should not be used for discrimination of monocytic lineage from granulocytic in in vitro differentiation cultures. The cause of the high CD14 expression in in vitro generated neutrophils is not clear, but it could be related to the upregulating effect of colony simulating factors (CSFs) on CD14 expression (Wright, S. D., et al. 1991, *J. Exp. Med.* 173:1281-1286.). The hESC-derived neutrophils expressed neutrophil-specific genes AZU1 (azurocidin 1), ELANE (elastase 2), CTSG (cathepsin G), and PRTN3 (proteinase 3; FIG. 4C). The level of PRTN3 expression in hESC-derived neutrophils was much higher as compared with that in peripheral blood and CD34$^+$ cell-derived neutrophils, while AZU expression was notably lower (FIG. 8). The majority of the cells also expressed lactoferrin (the constituent of neutrophil granules) as detected by flow cytometry (FIG. 4A). In response to PMA, hESC-derived neutrophils characteristically produced superoxide at a level comparable to somatic CD34+ cell-derived neutrophils, but lower as compared with freshly isolated peripheral blood neutrophils (FIG. 4F). In addition, hESC-derived neutrophils were capable of ingesting zymosan and E. coli particles (FIG. 4E) and showed a chemotactic response to N-formyl-Met-Leu-Phe (fMLP) (FIG. 4H). However, we noted decreased chemotactic response of hESC-derived neutrophils in comparison with somatic neutrophils due to an increase in spontaneous migration.

When CD235a/CD41a−CD34+CD45+ cells were cultured on OP9 in serum-containing medium with IL-3 and IL-5, an essentially pure population of eosinophils was generated. Characteristically, hESC-derived eosinophils had abundant cytoplasm filled by numerous coarse, orange-red granules of uniform size and a classic 2-lobed nucleus (FIG. 3E). The hESC-derived eosinophils, similar to peripheral blood eosinophils (Tachimoto, H., Bochner, B. S. 2000. *Chem. Immunol.* 76:45-62.), lacked CD16, CD64, CD66b, CD123 (IL-3R), and FceRII (CD23) expression (FIG. 4B). Intracellular and cytochemical staining revealed expression of two of the eosinophil granule proteins, major basic protein (MBP; crystalloid core component) and eosinophil peroxidase (EPO; one of the matrix components of granules) in hESC-derived eosinophils (FIG. 4B and FIG. 3F). mRNA encoding the Charcot-Leyden crystal (CLC) protein (lysophospholipase or galectin 10) was also detected (FIG. 4D). No significant differences were observed in the level of CLC and EPO expression in hESC- and somatic CD34+ cell-derived eosinophils (FIG. 8). Reactive oxygen species were produced in hESC-derived eosinophils stimulated with PMA. Furthermore, $O_2^-$ production from hESC-eosinophils was similar to that from adult CD34+ cell-derived eosinophils (FIG. 4G). However, hESC-derived eosinophils showed a decreased chemotactic response to fMPL when compared with their somatic counterpart (FIG. 4I). Whereas we employed the OP9 feeder in the granulocyte differentiation system, eosinophils could also be efficiently generated in feeder-free conditions with the use of IL-5. Neutrophils could also be generated in feeder-free conditions, although with much lower efficiency (data not shown).

Figure 3:
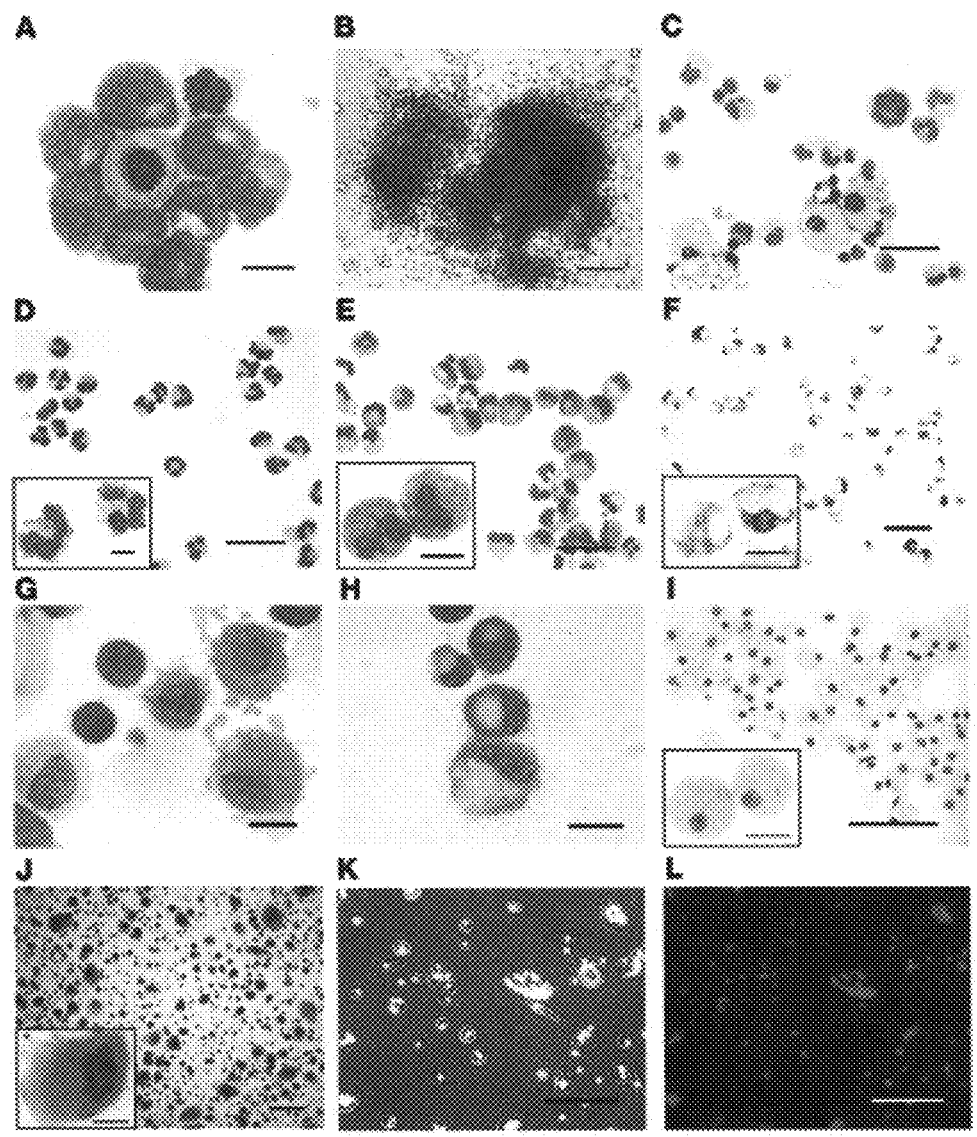
FIG. 3 shows morphology and cytochemical features of H1 hESC-derived myeloid progenitors and differentiated myelomonocytic cells. (A) Wright-stained cytospins of H1-derived CD235a/CD41a$^-$CD45$^+$ cells after 2 days expansion with GM-CSF (scale bar: 10 μm). (B) Typical GEMM-CFC generated from day 2 GM-CSF-expanded cells (scale bar: 200 μm). Wright-stained cytospins of GEMM-CFC (scale bar: 40 μm) (C), hESC-derived mature neutrophils (scale bar: 25 μm; inset, 5 μm) (D), eosinophils (scale bar: 40 μm; inset, 10 μm) (E), CD1a$^+$ cells isolated from DC (scale bar: 10 μm) (G) and LC (scale bar: 10 μm) (H) cultures, and macrophages (scale bar: 100 μm; inset, 20 μm) (I). (F)

Macrophages were generated by culture of CD235a/CD41a−CD34+CD45+ cells in serum-containing medium with M-CSF and IL-1β. Cells obtained in these conditions had typical macrophage morphology (FIG. 3I) and expressed CD115 (M-CSFR), CD163, CD14, and CD68 (FIG. 5C). DCs were obtained through culture of CD235a/CD41a+CD45+ cells in serum-free medium with the addition of GM-CSF, IL-4, and TNF-α, while GM-CSF, TNF-α, and TGF-β were used to generate LCs. After 9 days, 20.2%±3.2% CD1a+ cells were detected in DC cultures and 10.3%±2.0% CD1a+ cells in LC cultures. Isolated CD1a+ DCs and LCs showed dendritic projections and veils typical of cells of dendritic lineage (FIGS. 3, G and H). In contrast to DCs, CD1a+ cells in LC cultures expressed intracellular Langerin (CD207; a C-type lectin of LCs), E-cadherin, and cutaneous lymphocyte-associated antigen (CLA); had a CD14−DC-SIGN−CD11b$^{lo}$ phenotype (FIG. 5B); and were lacking in CCL17 and CCL13 chemokines, IRF4 transcription factor, and matrix metalloprotease MMP12 transcripts (FIG. 5F), consistent with the LC nature of these cells (Santegoets, S. J., et al. 2008, *J. Leukoc. Biol.* 84:143-151. Valladeau, J., Saeland, S. 2005, *Semin. Immunol.* 17:273-283.). Both DCs and LCs displayed a phenotype typical of antigen-presenting cells, including expression of costimulatory molecules (CD80, CD86, and CD40) and a high level of HLA-DR (FIG. 5, AC). However, DCs and LCs could be distinguished from macrophages by CD1a$^{hi}$CD1c+HLA-DR$^{hi}$CD14$^{lo/-}$CD115− CD163− phenotype (FIG. 5, AC). hESC-derived macrophages, DCs, and LCs were functional, as demonstrated by their ability to uptake and process a self-quenched conjugate of ovalbumin (DQ-OVA) (FIG. 5D) and allostimulate naive and adult T cells in mixed lymphocyte reaction (FIG. 5E). As expected, macrophages induced a much weaker alloresponse than did DCs and LCs.

The addition of vitamin D3 to hESC-derived CD235a/CD41a−CD34+CD45+ cells cultured in non-adherent conditions in the presence of GM-CSF was the most critical factor for inducing and expanding osteoclast precursors. When osteoclast precursors were transferred into conventional cell culture plates and cultured in the presence of vitamin D3 and RANKL for an additional 7-14 days, a pure population of mature tartrate-resistant acid phosphatase-positive (TRAP-positive) multinucleated osteoclasts was generated (FIG. 3, J-L). As demonstrated by PCR and flow cytometry, hESC-derived osteoclasts expressed vitronectin (VTNR) and calcitonin receptors (CALCR), cathepsin K (CTSK), and RANK (FIGS. 6, A and B). While no significant differences were found in expression of RANK, CALCR, and VTNR by hESC- and CD34+ cell-derived osteoclasts, the level of CTSK expression was remarkably higher in osteoclasts generated from hESCs (FIG. 8). Osteoclasts generated from hESCs, in contrast to macrophages, were capable of resorbing mineralized matrix (FIG. 6, C-F).

All types of myeloid cells were also generated from H9 hESCs, but the yield was less than that obtained from H1 hESCs, primarily due to less efficient generation of lin−CD34+CD43+CD45+ cells in H9/OP9 cocultures (Table 1).

TABLE 1

Generation of CD235a/41a−CD45+ cells and differentiated myeloid cells from H9 hESCs, and iPS(foreskin)-1 and iPS(SK46)M4-10 hiPSCs.

| | Yield 10$^{6}$* | | |
|---|---|---|---|
| Cell type | H9 | iPS(foreskin)-1 | iPS(SK46)M4-10 |
| GM-CSF expanded CD235a/41a−CD45+ cells | 0.3 ± 0.01 | 1.5 ± 0.1 | 0.9 ± 0.1 |
| Neutrophils | 6.8 ± 0.9 | 63.0 ± 8.4 | 61.3 ± 14.0 |
| Eosinophils | 46.6 ± 4.1 | 455.3 ± 65.8 | 312.8 ± 18.2 |
| Dendritic cells | 0.6 ± 0.01 | 6.4 ± 1.1 | 4.7 ± 0.9 |
| Langerhans cells | 0.3 ± 0.01 | 0.9 ± 0.1 | 0.6 ± 0.1 |
| Macrophages | 1.5 ± 0.2 | 14.9 ± 1.5 | 9.0 ± 1.0 |
| Osteoclasts | 2.7 ± 0.2 | 17.2 ± 1.7 | 5.7 ± 0.6 |

*Yield was calculated as a total number of indicated types of cells obtained from one 10 cm dish of hESC/OP9 coculture. To initiate differentiation, hESC H9 (2.0 ± 0.2 × 10$^{6}$ cells), iPS(foreskin)-1 (1.5 ± 0.6 × 10$^{6}$ cells), or iPS(SK46)M4-10 (1.5 ± 0.1 × 10$^{6}$ cells) were collected from one 6 well plate and cocultured with OP9 for 9 days in one 10 cm dish. The 0.03 ± 0.01 × 10$^{6}$ (H9), 0.2 ± 0.1 × 10$^{6}$ (iPS(foreskin)-1), or 0.2 ± 0.1 × 10$^{6}$ (iPS(SK46)M4-10) lin−CD34+CD43+45+ cells were generated at day 9 of differentiation from one 10 cm dish of hESC or iPSC/OP9 coculture, respectively. The absolute number of CD235a/CD41a− CD45+ cells generated after expansion for 2 days with GM-CSF and mature myeloid cells generated from these expanded cells is shown.
Results are mean ± SE of 3 experiments.

Optimization of Differentiation Protocol to Increase Output of Mature Myeloid Cells and Generation of Mature Myelomonocytic Cells from hiPSCs.

The above-described studies demonstrated that lin−CD34+CD45+ myeloid progenitors with the potential to differentiate into almost the entire spectrum of myelomonocytic cells could be obtained from hESCs in sufficient quantities for differentiation, functional, and molecular studies. However, the total output of cells of macrophage/dendritic lineage using cells expanded with GM-CSF for 2 days was relatively low (Table 2). Since substantial GM-CSF-mediated expansion of CD45+ cells was observed by day 8 of differentiation, we assessed the differentiation potential of these cells in an attempt to scale up production. Indeed, on day 8, GM-CSF cells were capable of differentiation into macrophages and DCs, under conditions similar to that described above, with an apparent increase in yield of these cell types (Table 2). We also noted that maturation of day 8 cells into macrophages occurred much faster and required only 2-3 days of culture with M-CSF and IL-1β, instead of the 5-7 days required for cells expanded with GM-CSF for 2 days. In addition, DC and macrophage cultures obtained from day 8 cells contained the highest number of terminally differentiated cells, with only a few immature myeloid cells present. The percentage of CD1a$^+$ cells in DC cultures from day 8 GM-CSF-expanded cells exceeded 70%, in contrast to only 20% CD1a$^+$ cells seen in cultures from day 2 expanded cells. However, we were unable to generate LCs from myeloid cells expanded with GM-CSF for a period longer than 2 days.

TABLE 2

Yield of H1 hESC-derived CD235/CD41a$^-$CD45$^+$ cells after 2 or 8 days expansion with GM-CSF and mature myeloid cells obtained from expanded cells

| Cell type | Yield (×10$^6$)$^A$ GM-CSF expansion | |
|---|---|---|
| | 2 days | 8 days |
| CD235a/CD41a$^-$CD45$^+$ cells | 1.3 ± 0.1 | 31.7 ± 4.3 |
| Neutrophils | 59.3 ± 4.7 | 15.9 ± 1.2 |
| Eosinophils | 266.9 ± 34.7 | 30.8 ± 11.2 |
| DCs | 2.2 ± 0.1 | 9.5 ± 0.6 |
| LCs | 0.5 ± 0.1 | N/A |
| Macrophages | 1.1 ± 0.1 | 17.9 ± 3.6 |
| Osteoclasts | 5.8 ± 0.3 | 25.1 ± 3.0 |

$^A$Yield was calculated as total number of indicated types of cells obtained from one 10-cm dish of hESC/OP9 coculture. To initiate differentiation, H1 hESCs (1.2 × 10$^6$ ± 0.02 × 10$^6$ cells) were collected from one 6-well plate and cocultured with OP9 for 9 days in one 10-cm dish. The 0.18 × 10$^6$ ± 0.01 × 10$^6$ lin$^-$CD34$^+$CD43$^+$CD45$^+$ cells were generated at day 9 of differentiation from one 10-cm dish of hESC/OP9 coculture. The absolute numbers of CD235a/CD41a$^-$CD45$^+$ cells generated after expansion for 2 or 8 days with GM-CSF and differentiated cells generated from these expanded cells are shown.
N/A, not applicable (no LCs could be generated from day 8 GM-CSF expanded cells).
Results are mean ± SEM of 5-10 experiments.

While day 8 GM-CSF expanded CD235a/CD41a$^-$CD45$^+$ cells were still capable of differentiation into neutrophils and eosinophils, the cell output was lower as compared with cells obtained after 2 days GM-CSF expansion (Table 2), probably reflecting the relative decrease in granulocytic potential with time. Thus, we concluded that expansion of CD235a/CD41a$^-$CD45$^+$ cells with GM-CSF for 2 days provides optimal yield of granulocytes, while expansion of the same cells with GM-CSF for 8 days maximizes yield of DCs and macrophages.

Next, we applied our protocol to generate mature myelomonocytic cells from hiPSCs. In this study, we used 2 hiPSC lines, iPS(foreskin)-1 and iPS(SK46)-M-4-10, which were obtained through reprogramming of neonatal foreskin fibroblasts with POU5F1, SOX2, and NANOG and adult SK46 fibroblasts with POU5F1, SOX2, NANOG, and LIN28 transcription factors (Yu, J., et al. 2007, *Science.* 318:1917-1920. Choi, K., et al. 2009, *Stem Cells.* 27:559-567.). We were able to obtain neutrophils, eosinophils, macrophages, DCs, LCs, and osteoclasts from both iPS(foreskin)-1 and iPS(SK46)-M-4-10 (FIGS. 9 and 10). The yield of differentiated cells from these hiPSC lines was comparable to that obtained from H1 hESCs (Table 1). These findings support our prior conclusion that the pattern and requirements for hematopoietic differentiation from hiPSCs and hESCs are very similar (Choi, K., et al. 2009, *Stem Cells.* 27:559-567.). As we previously noted, both endogenous and retrovirally introduced pluripotency genes were silenced in hiPSC-derived multipotent hematopoietic cells (Choi, K., et al. 2009, *Stem Cells.* 27:559-567.), and no reactivation of these genes was observed in terminally differentiated cells (FIG. 11).

Discussion

Several studies have reported generation of neutrophils, esosinophils, monocyte/macrophages, DCs, and osteoclasts from mouse ES cells, human bone marrow cells, or mobilized peripheral blood hematopoietic progenitors/stem cells (Lieber, J. G., et al. 2004, *Blood.* 103:852-859. Hamaguchi-Tsuru, E., et al. 2004, *Br. J. Haematol.* 124:819-827. Fairchild, P. J., et al. 2000, *Curr. Biol.* 10:1515-1518. Senju, S., et al. 2003, *Blood.* 101:3501-3508. Yamane, T., et al. 1997, *Blood.* 90:3516-3523. Hino, M., et al. 2000, *Br. J. Haematol.* 109:314-321. Haylock, D. N., et al. 1992, *Blood.* 80:1405-1412. Smith, S. L., et al. 1993, *Exp. Hematol.* 21:870-877. Rosenberg, H. F., Dyer, K. D., Li., F. 1996, *Exp. Hematol.* 24:888-893. Thavarajah, M., et al. 1991, *Biochem. Biophys. Res. Commun.* 176:1189-1195. MacDonald, B. R., et al. 1987, *Endocrinology.* 120:2326-2333. Caux, C., et al. 1996, *J. Exp. Med.*). Recently, methods for obtaining neutrophils, macrophages, and DCs from hESCs have been described as well (Karlsson, K. R., et al. 2008, *Hematol.* 36:1167-1175. Slukvin, L I., et al. 2006, *J. Immunol.* 176:2924-2932. Su, Z., et al. 2008, *Clin. Cancer Res.* 14:6207-6217. Senju, S., et al. 2007, *Stem Cells.* 25:2720-2729. Saeki, K., et al. 2008, *Stem Cells.* 27:59-67.). However, the progenitors giving rise to cells of myeloid lineage are often obscure, especially in differentiation systems employing ES cells. The major advantage and novelty of the differentiation system described in the present work is that it is based on generation and expansion of prospectively identifiable lin$^-$CD34$^+$CD43$^+$CD45$^+$ multipotent hematopoietic progenitor from hESCs. This approach facilitates obtaining an essentially homogenous population of mature myeloid cells of a desired type and provides an opportunity to further refine the myeloid lineage fate map, trace myeloid lineage diversification, and create an in vitro model of leukemic transformation in humans using an hESC line engineered to conditionally express oncogenes. In addition, the efficiency of generation of mature myelomonocytic cells by our method was much higher as compared with that achieved with previously described methods. For example Saeki at al. (Saeki, K., et al. 2008, *Stem Cells.* 27:59-67.) were able to obtain only 10$^6$ neutrophils per 10$^6$ hESCs, while our methods made it possible to generate up to 60×10$^6$ neutrophils or up to 270×10$^6$ eosinophils per 10$^6$ hESCs. The major advantage of the Saeki method is that xenogenic feeder cells are not required for differentiation, because it occurs within hESC-derived adherent sac-like structures. However, the Saeki method uses 6 cytokines for neutrophil generation; requires 40 days of culture to obtain a population of cells containing only 50% neutrophils; and has limited utility, since authors were able to generate neutrophils from only 1 of 3 tested hESC lines. Because hESC-derived lin$^-$CD34$^+$CD43$^+$CD45$^+$ myeloid progenitors generated from hESCs in OP9 coculture possessed substantial myeloid colony forming and in vitro expansion potential, we found that the most critical limiting factor in scaling up production of mature cells from undifferentiated pluripotent stem cells was the efficiency of generation of these myeloid progenitors from hESCs.

Previously, we reported that hESC-derived myeloid cells expanded with GM-CSF could be used to generate DCs (Slukvin, Vodyanik, M. A., Thomson, J. A., Gumenyuk, M. E., Choi, K. D. 2006, *J. Immunol.* 176:2924-2932.). In the present work, we defined the phenotype of hESC-derived myeloid progenitors and demonstrated that lin$^-$CD34$^+$CD43$^+$CD45$^+$ cells, after expansion with GM-CSF, could generate almost the entire spectrum of myelomonocytic cells, including neutrophils, eosinophils, macrophages, DCs, LCs, and osteoclasts. The protocol for DC differentiation was also optimized by using a higher concentration of GM-CSF (200 ng/ml) in expansion medium and a lower concentration of TNF-α (2.5 ng/ml) in the DC differentiation cocktail to improve the yield of functional DCs.

Despite our success in defining conditions for the generation neutrophils, eosinophils, macrophages, DCs, LCs and osteoclasts, our multiple attempts to generate basophils from hESC-derived lin$^-$CD34$^+$CD43$^+$CD45$^+$ cells failed. Although we were able to differentiate peripheral blood CD34$^+$ cells into basophils in the presence of IL-3 and SCF (FIG. 12), any cytokine combinations known to induce basophil differentiation from somatic CD34$^+$ cells (Arock, M., et al. 2002, *J. Leukoc. Biol.* 71:557-564) were not sufficient to induce basophil differentiation from hESC-derived myeloid progenitors. We have not yet determined whether basophil differentiation from hESCs requires a particular, not-yet-identified cytokine cocktail or whether they arise from different multipotent progenitors such as lin$^-$CD34$^+$CD43$^±$CD45$^-$ cells that emerge in hESC/OP9 coculture before CD45$^+$ cells can be detected (Vodyanik, M. A., et al. 2006, *Blood* 108: 2095-2105). In addition, we noted that hESC-derived myeloid progenitors are easily skewed to differentiate toward eosinophils. To obtain a pure population of neutrophils, it was essential to limit cytokine combination to G-CSF alone. The addition of other cytokines, such as IL-3, IL-6, or GM-CSF, in an attempt to improve neutrophil yield resulted in production of a mixture of eosinophils and neutrophils, with eosinophils often predominating.

With the exception of neutrophils, which are numerous in peripheral blood and easy to obtain, other types of human myelomonocytic cells are present in tissues in small quantities and are often inaccessible. Eosinophils constitute only 1%-3% of peripheral blood nucleated cells. DCs and osteoclasts are usually obtained from donor-derived CD34$^+$ hematopoietic progenitors or monocytes, which is a critically limiting factor for generation of sufficient numbers of cells for experimental purposes. The hESC-based approach described here provides a valuable alternative to existing methods for obtaining human myelomonocytic cells. Because hESCs are capable of self-renewal and large-scale expansion, a large number of myeloid precursors and terminally differentiated cells could be generated for not only functional studies, but potentially for therapeutic purposes. hESC-derived myeloid precursors can be also used for myelotoxicity screening of chemotherapeutic drugs, which is currently based on donor-derived bone marrow cells. The major advantage of the use of hESC-derived myeloid progenitors is the possibility for standardization of the myelotoxicity screening assay through elimination of variability related to various donor use.

Reprogramming somatic cells to the pluripotent state provides an unprecedented opportunity to generate immunologically compatible cells for cellular therapies. Recent achievements in the generation of vector- and transgene-free iPSCs brought this possibility closer to reality (Yu, J., et al. 2009 *Science*. 324:797-801. Zhou, H., et al. 2009, *Cell Stem Cell*. 4:381-384.). In addition, recent data demonstrating disease-specific changes in differentiated cells obtained from patient-specific hiPSCs (Ebert, A. D., et al. 2009, *Nature*. 457:277-280.) prove the utility of hiPSCs for the study of the mechanisms of diseases. The protocol described here could be used to generate mature myelomonocytic cells from hiPSCs obtained from patients with disorders of host defense in quantities sufficient for functional studies, as well as for drug screening.

Methods

Cell Lines, Cytokines, Growth Factors, and Monoclonal Antibodies.

H1 (NIH code WA01) and H9 (NIH code WA09) hESC lines (WiCell Research Institute) were maintained as undifferentiated cells in cocultures containing mouse embryonic fibroblasts (MEFs) (Amit, M., et al. 2000, *Dev. Biol.* 227:271-278.). iPS(foreskin)-1 hiPSC lines were obtained by reprogramming of newborn foreskin fibroblasts with POU5F1, SOX2, and NANOG (Yu, J., et al. 2007, *Science*. 318:1917-1920.). The iPS(SK46)-M-4-10 hiPSC line was obtained by reprogramming adult fibroblasts with POU5F1, SOX2, NANOG, and LIN28 (Choi, K., et al. 2009, *Stem Cells*. 27:559-567.). Both hiPSC lines were provided by James Thomson (University of Wisconsin-Madison). The hiPSCs were maintained in an undifferentiated state in coculture with MEFs essentially in the same conditions as hESCs (Amit, M., et al. 2000, *Dev. Biol.* 227:271-278.), but with a higher concentration of bFGF (100 ng/ml; PeproTech) (Yu, J., et al. 2007, *Science*. 318:1917-1920.). The mouse bone marrow stromal cell line OP9 was obtained from Tom Nakano (Research Institute for Microbial Diseases, Osaka University, Osaka, Japan). This cell line was maintained on gelatinized 10-cm dishes (BD Biosciences) in the OP9 growth medium consisting of α-MEM (Invitrogen) supplemented with 20% defined FBS (HyClone Laboratories). Sterile, recombinant, endotoxin- and pyrogen-free IL-1β, IL-3, IL-4, IL-5, M-CSF, TNF-α, TGF-β, and SCF were obtained from PeproTech; G-CSF (Neupogen) from Amgen; GM-CSF (Leukine) from Berlex Laboratories. fMLP, PMA, and vitamin D3 (1α,25-dihydroxyvitamin D3) were purchased from Sigma-Aldrich. The following monoclonal antibodies were used for flow cytometric analysis: CD10, CD11b, CD13, CD16, CD32, CD64, CD80, CD86, HLA-DR, MPO, lactoferrin (Invitrogen); CD115, CD163, Langerin (R&D Systems); CD1c, CD15, CD123, CD133, CD203c (Miltenyi Biotec); CD2, CD3, CD7, CD11c, CD14, CD19, CD23, CD24, CD31, CD33, CD34, CD38, CD40, CD41a, CD43 (clone 1G10), CD45, CD51/61, CD56, CD66b, CD90, CD117, DC-SIGN (CD209), CLA, CXCR4, MBP, CD235a (BD Biosciences); CD1a, E-cadherin (CD324), CD68, CD205 (BioLegend); FceRII (eBioscience); DC-LAMP (CD208), CD83 (Immunotech); mouse CD29 (AbD Serotec).

hESC and hiPSC Differentiation in OP9 Coculture and Expansion of Myeloid Progenitors.

Hematopoietic differentiation was induced by transferring the hESCs or hiPSCs onto OP9 feeders as we have previously described in detail (Vodyanik, M. A., et al. 2005, *Blood*. 105:617-626. Vodyanik, M. A., et al. 2007, *Curr. Protoc. Cell Biol. Chapter* 23, unit 23.6. Both references are incorporated by reference herein.). On day 9 of coculture, differentiated hESCs/hiPSCs were harvested by treatment with collagenase IV (Invitrogen; 1 mg/ml in α-MEM) for 20 minutes at 37° C., followed by treatment with 0.05% Trypsin-0.5 mM EDTA (Invitrogen) for 15 minutes at 37° C. After trypsin inactivation by FBS, cells were cultured in α-MEM containing 10% FBS and 200 ng/ml GM-CSF for 1-8 days to expand myeloid progenitors in T75 flasks coated with poly 2-hydroxyethyl methacrylate (pHEMA) to create a hydrophobic surface and prevent cell attachment. Subsequently, cells were spun over 20% Percoll (Sigma-Aldrich) to remove dead cells and cell aggregates as described previously in detail (Slukvin, I. I., et al. 2006, *J. Immunol.* 176:2924-2932. Vodyanik, M. A., et al. 2007 *Methods Mol. Biol.* 407:275-293. Both references are incorporated by reference herein.). To obtain a CD235a/CD41a$^-$CD45$^+$ population of cells enriched in multipotent myeloid progenitors, Percoll-isolated cells were depleted of erythro-megakaryocytic progenitors and contaminating OP9 cells by negative MACS selection using CD235a-PE, CD41a-PE, and mouse CD29PE Abs and anti-PE microbeads (Miltenyi Biotec). Subsequently, $CD45^+$ cells were isolated from the $CD235a/CD41a^-$ fraction by indirect magnetic-based sorting with anti-human CD45-FITC Abs (BD Biosciences) followed by anti-FITC microbeads (Miltenyi Biotec). Purity of isolated $CD235a/CD41a^-CD45^+$ fraction was more than 97% as verified by FACS analysis.

Directed Differentiation of Myeloid Lineages.

A schematic diagram of the differentiation protocol for obtaining progenitors and mature cells of myeloid lineage is presented in FIG. 1. GM-CSF expanded $CD235a/CD41a^-CD45^+$ cells were cultured on OP9 cells ($2.5 \times 10^4$ to $5.0 \times 10^4$ cells/3 ml/well of a 6-well plate) in Iscove's modified Dulbecco's medium (IMDM) (Invitrogen) containing 20% FBS and 100 ng/ml G-CSF for 8 days to generate neutrophils or 10 ng/ml IL-3 and 5 ng/ml IL-5 for 12-14 days to generate eosinophils. Macrophage, DC, and LC differentiation was performed in low-adherence conditions in pHEMA-coated flasks. For DC and LC differentiation, cells ($1 \times 10^6$ cells/5 ml/flask) were cultured in Stemline II serum-free hematopoietic stem cell expansion medium (Sigma-Aldrich) supplemented with 1% EX-CYTE (Millipore) and containing 20 ng/ml GM-CSF and 20 ng/ml IL-4 (DC cultures) or 20 ng/ml GM-CSF and 2.5 ng/ml TGF-β (LC cultures) for 7 days, with 2.5 ng/ml TNF-α added to DC cultures or 1 ng/ml TNF-α to LC cultures after the first medium change (day 3 of culture). Macrophages were obtained in cultures containing IMDM supplemented with 10% FBS, 20 ng/ml M-CSF, and 10 ng/ml IL-1β after 5-7 days of differentiation. Osteoclast differentiation was induced in 2 steps. First, osteoclast progenitors were expanded in α-MEM containing 10% FBS, 50 ng/ml GM-CSF, and 200 nmol vitamin D3 in pHEMA-coated flasks. After 5 days, cells were collected and cultured ($5 \times 10^4$ cells/3 ml/well) in α-MEM containing 10% FBS, 50 ng/ml GM-CSF, 200 nmol vitamin D3, and 10 ng/ml RANKL for an additional 14 days in conventional 6-well plates. For FACS analysis, osteoclasts were collected by treatment of cell cultures with PBS-based enzyme-free cell dissociation buffer (Invitrogen).

Isolation of Peripheral Blood Neutrophils and Generation of Myeloid Cells from Adult $CD34^+$ Progenitor Cells.

Peripheral blood samples from healthy adult donors were obtained using dextran sedimentation, Ficoll-Paque (Amersham Biosciences; GE Healthcare) centrifugation, and hypotonic lysis of contaminating erythrocytes, as previously described (Heit, B., Tavener, S., Raharjo, E., Kubes, P. 2002, *J. Cell Biol.* 159:91-102.). Frozen peripheral blood $CD34^+$ cells intended for final disposition were obtained from the University of Wisconsin Hematopoietic Stem Cell Laboratory with approval from the University of Wisconsin Institutional Review Board. Donors had previously signed an Institutional Review Board-approved consent. $CD34^+$ cells were cultured on OP9 cells in IMDM (Invitrogen) containing 20% FBS and 100 ng/ml G-CSF and 10 ng/ml IL-6 to generate neutrophils or 10 ng/ml IL-3 and 5 ng/ml IL-5 to generate eosinophils. To generate DCs, $CD34^+$ cells were cultured in Stemline II serum-free hematopoietic stem cell expansion medium (Sigma-Aldrich) supplemented with 1% EX-CYTE (Millipore) and containing 20 ng/ml GM-CSF, 20 ng/ml FLT3L, 20 ng/ml SCF, 20 ng/mL IL-4, and 2.5 ng/ml TNF-α in pHEMA-coated flasks. Similar culture conditions were used to generate LCs, except that the cytokine combination was modified to include 20 ng/ml GM-CSF, 20 ng/ml FLT3L, 20 ng/ml SCF, 1 ng/mL TNF-α, and 2.5 ng/ml TGF-β. DCs and LCs were purified from cultures using CD1a-based magnetic sorting as described above. For osteoclast and macrophage differentiation, somatic $CD34^+$ cells were cultured under the same conditions as the hESC-derived $CD235a/CD41a^-CD45^+$ cells described above.

Flow Cytometric Analysis.

Cells were prepared in PBS-FBS (PBS containing 0.05% sodium azide, 1 mM EDTA, and 2% FBS), supplemented with 2% normal mouse serum (Sigma-Aldrich), and labeled with a combination of monoclonal antibodies and 7-aminoactinomycin D (7-AAD) for dead cell exclusion. Intracellular staining was performed using FIX & PERM cell permeabilization reagents (Invitrogen). Samples were analyzed using a FACSCalibur flow cytometer (BD Biosciences) with CellQuest acquisition software (BD Biosciences). List mode files were analyzed by FlowJo software (Tree Star Inc.). Control staining with appropriate isotype-matched control mAbs (BD Biosciences) was included to establish thresholds for positive staining.

Clonogenic Progenitor Cell Assay.

Hematopoietic clonogenic assays were performed in 35-mm low-adherent plastic dishes (CELLSTAR; Greiner Bio-One) using 1 ml/dish of MethoCult $GF^+$ H4435 semisolid medium (StemCell Technologies) as previously described (Vodyanik, M. A., Bork, J. A., Thomson, J. A., Slukvin, I. I. 2005, *Blood.* 105:617-626. Vodyanik, M. A., Thomson, J. A., Slukvin, I. I. 2006, *Blood.* 108:2095-2105, Vodyanik, M. A., and Slukvin, I. I. 2007, *Curr. Protoc. Cell Biol.* Chapter 23, unit 23.6.). Colonies were scored after 14-21 days of incubation according to morphological criteria as E-CFC, GEMM-CFC, GM-CFC, G-CFC, and M-CFC.

Functional Analysis of Mature Myeloid Cells.

Superoxide production by hESC-derived neutrophils and eosinophils in response to 10 nM PMA (Sigma-Aldrich) was evaluated using PeroXOquant Quantitative Peroxide Assay Kit (Pierce, Thermo Scientific). Chemotactic activity was determined by using the modified Boyden method (Boyden, S. 1962, *J. Exp. Med.* 115:453-466.). Briefly, neutrophils or eosinophils were put on the PET membrane (3-μm pore size) in an HTS Multiwell Insert System (BD Biosciences) containing 10 nM fMLP (Sigma-Aldrich) in the lower chamber, and the number of cells that had moved across the filter membrane was quantified after 3 hours of incubation at 37° C. and 5% $CO_2$. FITC-conjugated *E. coli* and zymosan particles (Molecular Probes, Invitrogen) have been used to assess phagocytosis by FACS. To determine cell autofluorescence and nonspecific binding, we incubated cells with conjugated particles at 4° C. (negative controls). Ovalbumin uptake and processing were determined using a self-quenched conjugate of ovalbumin (DQ-OVA; Molecular Probes) as we described previously (Slukvin, I. I., et al. 2006, *J. Immunol.* 176:2924-2932. Incorporated by reference herein.). For determination of allogeneic stimulatory capacity, graded quantities ($1 \times 10^3$ to $3 \times 10^3$ cells/well) of macrophages, magnetically purified and irradiated (35 Gy) $CD1a^+$ DCs, or LCs were cocultured with $1 \times 10^5$ adult peripheral (AllCells) or cord blood (Cambrex) mononuclear cells in RPMI 1640 medium (Invitrogen) containing 5% human AB serum (Sigma-Aldrich) in 96-well flat-bottom plates. At 6 days of culture, the resulting proliferation of responder cells was evaluated based on incorporation of $[^3H]$thymidine (Sigma-Aldrich). To evaluate bone resorption capacity, osteoclasts or terminally differentiated macrophages (negative control) were cultured in α-MEM containing 10% FBS, 50 ng/ml GM-CSF, 200 nmol vitamin D3, and 5 ng/ml RANKL in BioCoat Osteologic Bone Cell Culture System (BD Biosciences), and calcium resorption was evaluated by von Kossa staining and morphologic analysis of osteologic discs after 7 days of culture according to the manufacturer's instructions.

Cytochemistry.

For TRAP staining, osteoclasts were washed with PBS and fixed with 10% glutaraldehyde for 15 minutes. TRAP was visualized using naphthol AS-MX phosphate (Sigma-Aldrich) as a substrate, with reaction of the product with Fast Violet B salt (Sigma-Aldrich) in TRAP buffer (0.05 M acetate buffer, 0.03 M sodium tartrate, 0.1% Triton X-100, pH 5.0) (Minkin, C. 1982, *Calcif. Tissue Int.* 34:285-290.). For EPO staining, cells were fixed in formalin/acetone and stained for 10 minutes in 0.1 M phosphate buffer, pH 8.0, containing 2 mM 3,3-diaminobenzidine tetrachloride (Sigma-Aldrich), 8 mM NaCN (Sigma-Aldrich), and 0.009% $H_2O_2$ (Ten, R. M., Pease, L. R., McKean, D. J., Bell, M. P., Gleich, G. J. 1989. Molecular cloning of the human eosinophil peroxidase. Evidence for the existence of a peroxidase multigene family. *J. Exp. Med.* 169:1757-1769.).

RT-PCR.

Total RNA was isolated from cells using TRI Reagent (Ambion) and treated with DNAse (Invitrogen) to remove potentially contaminating DNA. Conventional RT-PCR was performed from 1 µg of total RNA using SuperScript III First-Strand synthesis (Invitrogen) and MasterTaq PCR kit (Eppendorf). Real-time quantitative PCR (Q-PCR) was performed using the $RT^2$ SYBR Green/ROX qPCR Master Mix (SABiosciences) on an ABI Prism 7700 Sequence Detection System (Applied Biosystem). The PCR primers used are listed in Table 3. The expression level of selected genes was calculated relative to RPL13A as a reference gene using the following formula: relative expression=$2^{(Ct\ ref - Ct\ gene)}$ (Muller, P. Y., Janovjak, H., Miserez, A. R., Dobbie, Z. 2002, *Biotechniques*. 32:1372-1374, 1376, 1378-1379.).

TABLE 3

Primers used for analysis of hESC-derived myeloid cells

| Genes | Symbol | Sequences | SEQ ID NOs | PCR product size (bp) |
|---|---|---|---|---|
| Azurocidin | AZU1 | Forward: 5'-gac tgg atc gat ggt gtt ctc-3' | 1 | 188 |
| | | Reverse: 5'-cag agg aga gat cgg ctt ctt-3' | 2 | |
| Calcitonin receptor | CALCR | Forward: 5'-tgc ggt ggt att atc tct tgg-3' | 3 | 212 |
| | | Reverse: 5'-ttc cct cat ttt ggt cac aag-3' | 4 | |
| Cathepsin G | CTSG | Forward: 5'-ctc aat ata atc agc gga cc-3' | 5 | 453 |
| | | Reverse: 5'-cca gca gtt tga agc ttc tc-3' | 6 | |
| Cathepsin K | CTSK | Forward: 5'-aag aag aaa act ggc aaa ct-3' | 7 | 595 |
| | | Reverse: 5'-atc gtt aca ctg cac cat cg-3' | 8 | |
| Charcot-Leyden crystal protein | CLC | Forward: 5'-cta ctg tga caa tca aag ggc gac-3' | 9 | 308 |
| | | Reverse: 5'-agc ctc agg ctt gat tct atg gtc-3' | 10 | |
| Chemokine (C-C motif) ligand 13 | CCL13 | Forward: 5'-atg aca gca gct ttc aac ccc-3' | 11 | 451 |
| | | Reverse: 5'-ctc caa acc agc aac aag tca at-3' | 12 | |
| Chemokine (C-C mitif) ligand 17 | CCL17 | Forward: 5'-atg gcc cca ctg aag atg ctt-3' | 13 | 351 |
| | | Reverse: 5'-tga aca cca acg gtg gag gt-3' | 14 | |
| Elastase 2 | ELANE | Forward: 5'-atc aac gcc aac gtg cag-3' | 15 | 252 |
| | | Reverse: 5'-gat tag ccc gtt gca gac-3' | 16 | |
| Eosinophil peroxidase | EPO | Forward: 5'-gca tct gtc ccc agc cct-3' | 17 | 334 |
| | | Reverse: 5'-gaa ggg tcc gga ccg ctg-3' | 18 | |
| Interferon regulatory factor-4 | IRF4 | Forward: 5'-tcc cca cag agc caa gca taa ggt-3' | 19 | 436 |
| | | Reverse: 5'-agg gag cgg ccg tgg tga gca-3' | 20 | |
| Metallo proteinase 12 | MMP12 | Forward: 5'-ttt tgc ccg tgg agc tca t-3' | 21 | 400 |
| | | Reverse: 5'-ttc cca cgg tag tga cag ca-3' | 22 | |
| Proteinase-3 | PRTN3 | Forward: 5'-ctt gat cca ccc cag ctt cgt g-3' | 23 | 228 |
| | | Reverse: 5'-gca gaa gaa ggt gac cac ggt gac-3' | 24 | |
| Receptor activator $NF_KB$ | RANK | Forward: 5'-tta agc cag tgc ttc acg gg-3' | 25 | 497 |
| | | Reverse: 5'-acg tag acc acg atg atg tcg c-3' | 26 | |
| Ribosomal protein L13A | RPL13A | Forward: 5'-cct gga gga gaa gag gaa aga ga-3' | 27 | 126 |
| | | Reverse: 5'-ttg agg acc tct gtg tat ttg tca a-3' | 28 | |
| Vitronectin receptor | VTNR | Forward: 5'-gtt ggg aga tta gac aga gg-3' | 29 | 440 |
| | | Reverse: 5'-cta gag ggt caa gat gta gc-3' | 30 | |

Statistics.

The significance of differences between the mean values of the tested samples was determined by 2-tailed Student's t test for unpaired values. P values less than 0.05 were considered significant.

---

We claim:

1. A method of producing myeloid lineage cells, comprising the steps of (a) obtaining a population of mammalian pluripotent stem cells, wherein the stem cells are derived from mammalian embryos or are induced pluripotent stem cells, (b) inducing hematopoietic differentiation to obtain lin⁻CD34⁺CD43⁺CD45⁺CD38⁻ multipotent hematopoietic cells by co-culturing the mammalian pluripotent stem cells with stromal cells, (c) expanding and differentiating lin⁻CD34⁺CD43⁺CD45⁺CD38⁻ cells from step (b) by culture in the presence of GM-CSF to obtain CD34⁺CD43⁺CD45⁺CD38⁺ myeloid progenitors and (d) exposing the CD34⁺CD43⁺CD45⁺CD38⁺ myeloid progenitors resulting from step (c) to:
(i) G-CSF for 7-9 days, wherein a population of neutrophils is isolated;
(ii) IL-3 and IL-5 for 12-14 days wherein a population of eosinophils is isolated;
(iii) M-CSF and IL-1β for 1-8 days wherein a population of macrophages is isolated;
(iv) GM-CSF, 1α,25-dihydroxyvitamin D3 for 5-7 days, then GM-CSF, 1α,25-dihydroxyvitamin D3 and RANKL for 7-14 days, wherein populations of osteoclasts are isolated;
(v) GM-CSF and IL-4 for 7-9 days, TNF-α being added after day 3 of GM-CSF and IL-4 exposure, wherein a population of dendritic cells is isolated; or (vi) GM-CSF and TGF-β, TNF-α being added after day 3 of GM-CSF and TGF-β exposure, wherein a population of Langerhans cells is isolated.

2. The method of claim 1, wherein the pluripotent stem cells of step (a) form embryoid bodies during step (b).

3. The method of claim 1, wherein the stromal cells are selected from the group consisting of S17, AM20.1B4, UG26.1B6, FH-B-hTERT, primary stromal cells and OP9 mouse bone marrow stromal cells.

4. The method of claim 3, wherein the stromal cells are OP9 mouse bone marrow stromal cells.

5. The method of claim 1, wherein the cells of step (c) are cultured for 2-8 days.

6. The method of claim 1, wherein step (d) comprises exposing the expanded cells to G-CSF for 7-9 days wherein a population of neutrophils is isolated.

7. The method of claim 6, wherein G-CSF is present at 100±50 ng/mL.

8. The method of claim 1, wherein step (d) comprises exposing the expanded cells to IL-3 and IL-5 for 12-14 days wherein a population of eosinophils is isolated.

9. The method of claim 8, wherein IL-3 and IL-5 are present at 10±5 ng/mL respectively.

10. The method of claim 5, wherein the cells of step (c) are cultured for 2 days, and step (d) comprises exposing the expanded cells to M-CSF and IL-1β for 1-8 days wherein a population of macrophages is isolated.

11. The method of claim 10, wherein M-CSF is present at 20±10 ng/mL and IL-1β is present at 10±5 ng/mL.

12. The method of claim 5, wherein the cells of step (c) are cultured for 8 days, and step (d) comprises exposing the expanded cells to M-CSF and IL-1β for 2-3 days wherein a population of macrophages is isolated.

13. The method of claim 12, wherein M-CSF is present at 20±10 ng/mL and IL-1β is present at 10±5 ng/mL.

14. The method of claim 1, wherein step (d) comprises exposing the expanded cells to GM-CSF and IL-4 for 7-9 days, TNF-α being added after day 3 of GM-CSF and IL-4 exposure, wherein a population of dendritic cells is isolated.

15. The method of claim 14, wherein GM-CSF is present at 20±10 ng/mL, IL-4 is present at 20±10 ng/mL and TNF-a is present at 2.5±1 ng/mL.

16. The method of claim 1, wherein step (d) comprises exposing the expanded cells to GM-CSF and TGF-β, TNF-α being added after day 3 of GM-CSF and TGF-β exposure, wherein a population of Langerhans cells may be isolated.

17. The method of claim 16, wherein GM-CSF is present at 20±2 ng/mL, TGF-β is present at 5±2.5 ng/mL and TNF-a is present at 1±0.5 ng/mL.

18. method of claim 1, wherein step (d) comprises exposing the expanded cells to GM-CSF and 1α,25-dihydroxyvitamin D3 for 5-7 days, then GM-CSF, 1α,25-dihydroxyvitamin D3 and RANKL for 7-14 days, wherein a population of osteoclasts is isolated.

19. The method of claim 18, wherein GM-CSF is present at 100±50 ng/mL for the first 5-7 days and 50±25 ng/mL for the last 7-14 days, 1α,25-dihydroxyvitamin D3 is present at 200+100 nmol and RANKL is present at 10±5 ng/mL.

20. The method of claim 18, wherein 1α,25-dihydroxyvitamin D3 is substituted with vitamin D3 like compounds selected from the group consisting of calcitriol, calcidiol, 19-nor-(20S)- 1α,25-dihydroxyvitamin D3, and 22-Oxacalcitriol.

21. The method of claim 1, wherein 1α,25-dihydroxyvitamin D3 is added to step(c), and step (d) comprises exposing the expanded cells to GM-CSF, 1α,25-dihydroxyvitamin D3 for 5-7 days, then GM-CSF, 1α,25-dihydroxyvitamin D3 and RANKL for 7-14 days, wherein populations of osteoclasts are isolated.

22. The method of claim 21, wherein 1α,25-dihydroxyvitamin D3 is substituted with vitamin D3 like compounds selected from the group consisting of calcitriol, calcidiol, 19-nor-(20S)- 1α,25-dihydroxyvitamin D3, and 22-Oxacalcitriol.

23. The method of claim 1, wherein the mammal is a human.

24. A method of producing myeloid progenitors, comprising the steps of (a) obtaining a population of mammalian pluripotent stem cells, wherein the stem cells are derived from mammalian embryos or are induced pluripotent stem cells (b) inducing hematopoietic differentiation to obtain lin$^-$CD34$^+$CD43$^+$CD45$^+$CD38$^-$ multipotent hematopoietic cells by co-culturing the mammalian pluripotent stem cells with stromal cells, and (c) expanding and differentiating lin$^-$CD34$^+$CD43$^+$CD45$^+$CD38$^-$ cells from step (b) by culture in the presence of GM-CSF, whereby CD34$^+$CD43$^+$CD45$^+$CD38$^+$ myeloid progenitors are produced.

* * * * *

UNITED STATES PATENT AND TRADEMARK OFFICE
CERTIFICATE OF CORRECTION

PATENT NO. : 8,846,395 B2
APPLICATION NO. : 12/586600
DATED : September 30, 2014
INVENTOR(S) : Igor I. Slukvin, Kyung-Dal Choi and Maksym A. Vodyanyk It is certified that error appears in the above-identified patent and that said Letters Patent is hereby corrected as shown below:

In the Specification

Column 8, line 46    -    "CD11a" should be --CD1a--

Column 16, line 21    -    "Tom" should be --Toru--

Signed and Sealed this
Thirtieth Day of June, 2015

Michelle K. Lee
*Director of the United States Patent and Trademark Office*

```
                        SEQUENCE LISTING

<160> NUMBER OF SEQ ID NOS: 30

<210> SEQ ID NO 1
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 1
gactggatcg atggtgttct c                                             21

<210> SEQ ID NO 2
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 2
cagaggagag atcggcttct t                                             21

<210> SEQ ID NO 3
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 3
tgcggtggta ttatctcttg g                                             21

<210> SEQ ID NO 4
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 4
ttccctcatt ttggtcacaa g                                             21

<210> SEQ ID NO 5
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 5
ctcaatataa tcagcggacc                                               20

<210> SEQ ID NO 6
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 6
```

```
ccagcagttt gaagcttctc                                               20

<210> SEQ ID NO 7
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 7
aagaagaaaa ctggcaaact                                               20

<210> SEQ ID NO 8
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 8
atcgttacac tgcaccatcg                                               20

<210> SEQ ID NO 9
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 9
ctactgtgac aatcaaaggg cgac                                          24

<210> SEQ ID NO 10
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 10
agcctcaggc ttgattctat ggtc                                          24

<210> SEQ ID NO 11
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 11
atgacagcag ctttcaaccc c                                             21

<210> SEQ ID NO 12
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 12
ctccaaacca gcaacaagtc aat                                           23

<210> SEQ ID NO 13
<211> LENGTH: 21
<212> TYPE: DNA
<213> ORGANISM: Artificial Sequence
```

```
<220> FEATURE:
<223> OTHER INFORMATION: Synthetic oligonucleotide

<400> SEQUENCE: 13
atggccccac tgaagatgct t                                              21

<210> SEQ ID NO 14
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 14
tgaacaccaa cggtggaggt                                                20

<210> SEQ ID NO 15
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 15
atcaacgcca acgtgcag                                                  18

<210> SEQ ID NO 16
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 16
gattagcccg ttgcagac                                                  18

<210> SEQ ID NO 17
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 17
gcatctgctc ccagccct                                                  18

<210> SEQ ID NO 18
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 18
gaagggtccg gaccgctg                                                  18

<210> SEQ ID NO 19
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 19
tccccacaga gccaagcata aggt                                           24
```

<210> SEQ ID NO 20
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 20
agggagcggc cgtggtgagc a                                             21

<210> SEQ ID NO 21
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 21
ttttgcccgt ggagctcat                                                19

<210> SEQ ID NO 22
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 22
ttcccacggt agtgacagca                                               20

<210> SEQ ID NO 23
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 23
cttgatccac cccagcttcg tg                                            22

<210> SEQ ID NO 24
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 24
gcagaagaag gtgaccacgg tgac                                          24

<210> SEQ ID NO 25
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 25
ttaagccagt gcttcacggg                                               20

<210> SEQ ID NO 26
<211> LENGTH: 22
<212> TYPE: DNA
<213> ORGANISM: Artificial Sequence
<220> FEATURE:
<223> OTHER INFORMATION: Synthetic oligonucleotide

```
<400> SEQUENCE: 26
acgtagacca cgatgatgtc gc                                    22

<210> SEQ ID NO 27
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 27
cctggaggag aagaggaaag aga                                   23

<210> SEQ ID NO 28
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 28
ttgaggacct ctgtgtattt gtcaa                                 25

<210> SEQ ID NO 29
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 29
gttgggagat tagacagagg                                       20

<210> SEQ ID NO 30
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 30
ctagtgggtc aagatgtagc                                       20
```